US006271443B1

(12) United States Patent
Stalker et al.

(10) Patent No.: US 6,271,443 B1
(45) Date of Patent: Aug. 7, 2001

(54) COTTON AND RICE CELLULOSE SYNTHASE DNA SEQUENCES

(75) Inventors: David M. Stalker, Woodland; Julie R. Pear; Deborah Delmer, both of Davis, all of CA (US)

(73) Assignee: Calgene LLC, Davis, CA (US)

( * ) Notice: Subject to any disclaimer, the term of this patent is extended or adjusted under 35 U.S.C. 154(b) by 0 days.

(21) Appl. No.: 08/960,048

(22) Filed: Oct. 29, 1997

Related U.S. Application Data

(60) Provisional application No. 60/029,987, filed on Oct. 29, 1996.

(51) Int. Cl.[7] .............................. A01H 5/00; C12N 5/14; C12N 15/29; C12N 15/52; C12N 15/82

(52) U.S. Cl. ...................... 800/298; 435/320.1; 435/419; 536/23.2; 536/23.6

(58) Field of Search .................................. 435/69.1, 419, 435/320.1, 468; 536/23.2, 23.6; 800/278, 286, 298, 314

(56) References Cited

U.S. PATENT DOCUMENTS 5,122,466 6/1992 Stomp et al. .
5,495,070 2/1996 John .

FOREIGN PATENT DOCUMENTS

WO 91/13988 9/1991 (WO) .
WO 98/00549 8/1998 (WO) .

OTHER PUBLICATIONS

Valla S, et al. Cloning of a gene involved in cellulose biosynthesis in Acetobacter xylinum: Complementation of cellulose–negative mutants by the UDPG pyrophosphorylase structural gene. Mol. Gen. Genet. 217:26–30, 1989.*

Matthysse AG, et al. "Genes required for cellulose sythesis in Agrobacterium tumefaciens." J. Bacteriol. 177: 1069–1075, Feb. 1995.*

Stam M, et al. "The silence of genes in transgenic plants." Ann. Bot. 79: 3–12, 1997.*

Koziel MG, et al. "Optimizing expression of transgenes with an emphasis on post–transcriptional events." Plant Mol. Biol. 32: 393–405, 1996.*

Smith CJS, et al. "Antisense RNA inhibition of polygalacturonase gene expression in transgenic tomatoes." Nature 334: 724–726, Aug. 25, 1988.*

De Block, M. "The cell biology of plant transformation: Current state, problems, prospects and the implications for plant breeding." Euphytica 71: 1–14, 1993.*

Lal SK, et al. "Cloning and characterization of an anaerobically induced cDNA encoding glucose–6–phosphate isomerase from maize." Plant Physiol. 108: 1295–1296, Jul. 1995.*

Penger A, et al. "cDNA sequence for the plastidic phosphoglucomutase from Spinicia oleracea (L.)." Plant Physiol. 105: 1439–1440, Aug. 1994.*

Amor, Et Al., "Evidence for a Cyclic Diguanylic Acid–Dependent Cellulose Synthase in Plants," The Plant Cell, 10th ed., American Society of Plant Physiologists, p. 989–995, (Aug. 9, 1991).

Martin, Et Al., "Expression of an Arabidopsis sycrose synthase gene indicates a role in metabolization of sucrose both during phloem loading and in sink organs," The Plant Journal, vol. 4 (No. 2), p. 367–377, (Aug. 20, 1993).

Martin, Et Al., "Expression of an Arabidopsis Sucrose synthase Gene Indicates a role in Metabolization of Sucrose both during Phloem loading and in sink organs," EMBL Seq. data library, p. X70990, (Dec. 28, 1993).

Delmar, Et Al., "Cellulose Biosynthesis," The Plant Cell, American Society of Plant Physiologists , p. 987–1000, (Aug. 7, 1995).

Pear, Et Al., "Higher plants contain homologs of the bacterial celA genes encoding the catalytic subunit of cellulose synthase," Plant Biology/Proc. Natl. Acad of Sci. USA, p. 12637–1264, (Aug. 10, 1996).

* cited by examiner

*Primary Examiner*—Amy J. Nelson

(57) ABSTRACT

Provided are two plant cDNA clones that are homologs of the bacterial CelA genes that encode the catalytic subunit of cellulose synthase, derived from cotton (*Gossypium hirsutum*).

13 Claims, 18 Drawing Sheets

```
G HIRSUTUM CELA-1       1 MMESGV-----PVCHTCGEHVGLNVNGEPFVACHE-CNFPICKSCFEYDLKEGRKACLR-------------------------CG
G HIRSUTUM CELA-2       -
O SATIVA CELA           -
A XYLINUM ACSAB         -
A XYLINUM BCSA          -
E COLI ORF F692         -
A TUMEFACIENS CELA      1 MCRCGRAVRSRPVCRP--GQLVVRRSPRPRSRNHSRCR-PLRLSVFPRPHRRVRHHCQRD LRWEPGRWIAVRWKAARSHRRFRRC-

                                   -G-

 56 SPYDENLL---DDVEKATGDQSTMAAHLNKS-QDVGIHARHISSVSTLDSEMAEDNGNSIWKNRVESWKEKKNK---------KKKPATTKVEREA
  1 ---------------------------------------------------GNVAWKERVDGWKLKQDKGAIPMTNGTSIAPSEGRGVGDI
  1 ----------------------------------------MPEVRSSTQSESGMSQWMGKI-----------LSIRGAGLTIGVFGLCALIA
  1 ----------------------------------------MSEVQSPVPAESRLDRFSNKI-----------LSLRGANYIVGALGLCALIA
  1 --------------------------------------ML---------------------------LWGVAL-----------
 83 -PFPRQLVWPVRERHRDAGDRPNQRERPPRDYHE:SEFKFPTPKRTE-----------------SFWMNKAITVIVWL---------LVSLCVL-A

                                   H-I

139 EIPPEQQMEDKP-APDASQPLSTIIPIPKSRLAPYRTVII-MRLIILGLFFHYRVTNPVDSAFGLWLTSVICEIWFA---FSWVLDQFPKWYPVNR
  -
 41 DASTDYNMEDALLNDETRQPLSRKVPLPSSRINPYRMVIV-LRLVVLSIFLHYRITNPVRNAYPLWLLSVICEIWFA---LSWILDQFPKWFPINR
 42 ATSVTLPPEQQLIVAFVCVVIFFIVGHKPSRRSQI-FLEV-LSGLVSLRYLTWRLTETLS--FDTWLQGLLGTMLLVAELYALMM-LFLSYFQTIA
 42 ATTVTLSINEQLIVALVCVLVFFIVGRGKSRRTQI-FLEV-LSALVSLRYLTWRLTETLD--FDTWIQGGLGVTLLMAELYALYM-LFLSYFQTIQ
  9 ------------------IVRRMPGRFSAL-MLIV-LSLTVSCRYIWWRYTSTLN--WDDPVSLVCGLILLFAETYAWIV-LVLGYFQVVW
152 IITMPVSLQTHLVATAISLILLATIKSFNGQ-GAWRLVALGFGTAIVLRYVYWRTTSTLPPV-NQLENFIPGFLLYLAEMYSVVM------LGLSL

                                   U-I ☆ P-CR

230 ETYIDRLSARYEREGEPDELAAVDFFVSTVDPLKEPPLITANTVLSILALDYPVDKVSCYISDDGAAMLTFESLVETADFARKWVPFCKKFSIEPR
  1 --------------------------------------------------------------ARRWVPFCKKHNVEPR
133 ETYLDRLALRYDREGEPSQLAAVDIFVSTVDPMKEPPLVTANTVLSILAVDYPVDKVSCYVSDDGAAMLTFDALAETSEFARKWVPFVKKYNIEPR
133 PLHRAPLPLP----PNPDEWPTVDIFVPTYN---EELSIVRLTVLGSLGIDWPPEKVRVHILDDGR-------------------------
133 PLHRAPLPLP----DNVDDWPTVDIFIPTYD---EQLSIVRLTVLGALGIDWPPDKVNVYILDDGV-------------------------
 77 PLNRQPVPLP----KDMSLWPSVDIFVPTYN---EDLNVVKNTIYASLGIDWPKDKLNIWILDDGG-------------------------
240 VIVSMPLPSRKTRPGSPDYRPTVDVFVPSYN---EDAELLANTLAAAKNMDYPADRFTVWLLDDGGSV-----------------------

326 APEFYFSQKIDYLKDKVQPSFVKERRAMKRDYEEYKIRINALVAKAQKTPDEGWTMQDGTSWPGNNPRDHPGMIQVFLGYSGARDIEGNELPRLVY
 29 APEFYFNEKIDYLKDKVHPSFVKERRAMKREYEEFKVRINALVAKAQKKPEEGWVMQDGTPWPGNNTRDHPGMIQVYLGSAGALDVDGKELPRLVY
229 APEWYFSQKIDYLKDKVHPSFVKDRRAMKREYEEFKVRINGLVAKAQKVPEEGWIMQDGTPWPGNNTRDHPGMIQVFLGHSGGLDTEGNELPRLVY
192 -------------------------RPEFAAFAAECGAN---------------------------------------------------Y
192 -------------------------RPEFEQFAKDCGAL---------------------------------------------------Y
136 -------------------------REEFRQFAQNVGVK---------------------------------------------------Y
305 ---------------QKRNAANIVEAQAAQRRHEELKKLCEDLDVR--------------------------------------------Y
```

FIGURE 3A

IH-2 U-2 G HVR IH-3 U-3 G U-4

FIGURE 3B

```
                                                                                              -G-
773 GKFIIPTLSNLASVLFLGLFLSIIVTAVLELRWSGVSIEDLWRNEQFWV-IGGVSAHLFAVFQGFLKMLAGIDTNFTVTAKAAD-DADFGEL----
499 GKFIIPTLSNLTSVWFLALFLSIIATGVLELRWSGVSIQDWWRNEQFWV-IGGVSAHLFAVFQGLLKVLAGVDTNFTVTAKAAD-DTEFGEL----
681 GKFIIPEISNFASIWFISLFISIFATGILEMRWSGVGIDEWWRNEQFWV-IGGISAHLFAVFQGLLKVLAGIDTNFTVTSKASDEDGDFAEL----
427 GQNIIAA-SPLALLAYAIPHM--F-HAVG----TASKINKGWRYS-FWSEVYETTMALFLVRVTIVTLLSPSRGKFNVTDKGGLLEKGYFDLGAVY
427 GQNIIAA-SPLAVLAYAIPHM--FSHSIA----TAAKVNKGWRYS-FWSEVYETTMALFLVRVTIITLMFPSKGKFNVTEKGGVLEEEEFDLGATY
471 HAYIIYA-PALMIALFVLPHM--I-HASL----TNSKIQGKYRHS-FWSEIYETVLAWYIAPPTLVALINPHKGKFNVTAKGGLVEEEYVDWVISR
556 DLQIFVA-SGGEFLAYTAAYM--LVN-LM----MQNYLYGSFRWP-WISELYEYVQTVHLLPAVVSVIFNPGKPTFKVTAKDESIAEARLS-EISR

863 ----------------------YIVK-----------------WT--TLLIPPTTLLIV-NM----------------VGVVAGFSDALNKGYE--------
589 ----------------------YLFK-----------------WT--TLLIPPTTLIIL-NM----------------VGVVAGVSDAINNGYG--------
772 ----------------------YMFK-----------------WT--TLLIPPTTILI INL----------------VGVVAGISYAINSGYQ--------
514 PNIILGLIMFGGLARGVYELSF--GHLDQIAERAYLLNSAWAMLSLIIIILAAIAVGRETQQKRNSHRIPATIPVEVANADGS--------IIVTGVT
514 PNIIFAGIMTLGLLIGLFELTFHFNQLAGIAKRAYLLNCIWAMISLIIILLAAIAVGRETKQVRYNHRVEAHIPVTVYEAPVAGQPNTYHNATPGMT
458 PYIFLVLLNLVGVAVGIW--RYFYGPPTEML--TVVVSMVWVFYNLIVLGGAVAVSVESKQVRRSHRVEMTMPAAIAREDG--------HLFSCTV
642 PFFVIFALLLVAMAFAVWRI---YSE--PYKADVTLVVGGWNLLNLIFAGCALGVVSERGDKSASRRITVKRRCEVQLGGSDTW--------VPASI

899 --------------AWGPLF--------------------------GKVFFSF---WVILHL---YPFLKGLMGRQNR-------------TPTIV
625 --------------SWGPLF--------------------------GKLFFAF---WVILHL---YPFLKGLMGRQNR-------------TPTIV
808 --------------SWGPLF--------------------------GKLFFAF---WVIVHL---YPFLKGLMGRQNR-------------TPTIV
601 EDLSMGGAAVKM-SWPAKLSGPTPVYIRTVLDGEEL--ILPARIIRAGNGRGIFI----WTIDNLQQEFSVIRLVFGRADAWVDLGQ-LQGRPP--
610 QDVSMGGVAVHM-PWPDVSTGPVKTRIHAVLDGEEI--DIPATMLRCKNGKAVFT----WDNNDLDTERDIVRFVFGRADAWLQWNN-YEDDRPLR
542 QDFSDGGLGIKI-NGQAQILEGQKVNLLLKRGQQEY--VFPTQVARVMGNEVGLK----LMPLTTQQHIDFVQCTFARADTWALWQDSYPEDKPLE
726 DNVSVHGLLINIFDSATNIEKGATAIVKVKPHSEGVPETMPLNVVRTVRGEGFVSIGCTFSPQRAVDHRLIADLIFANSEQWSEFQRVRRKKP---

936 VLWSVLLASVFSLVW----------------------VRINPFVSTADSTTVS----QSCISIDC     974
662 VLWSILLASIFSLVW----------------------VRIDPFLPKQTGPVL-----KQC-GVE      697
845 VVWAILLASIFSLLW----------------------VRIDPFTTRVTGPDT-----QTC-GINC     881
687 -----------------AAQPHG-HGSQRQGPVPFKW------R----YRPSQFPNQAFGWQCPV     723
698 SLWSLL-LSIKALFRKKGKMMANS-RPKRKPLALPVER------REPTTIQSGQTQEGKISRA-AS   754
631 SLLDILKLGFRG-YRHLAEFAPSSVKGIFRVLTSLVSWVVSFIPPRPERSETAQPSDQALAQQ      692
819 ------------GLIPGTAIFLAIALFQTQRGLY--------YLVRARRPAPKSAKPVGAVK       860
```

FIGURE 3C

```
CGAAATTAAC CCTCACTAAA GGGAACAAAA GCTGGAGCTC CACCGCGGTG GCGGCCGCTC   60
TAGAACTAGT GGATCCCCCG GGCTGCAGGA ATTCGGCACG AGGGTTAGCA TATTGTTTGT  120
AGCATTGGGT TTTTTTCTCA AGGAAGAAGA AGGAGAAAGA TAAGTACTTT TTTTGAGAAT  180
GATGGAATCT GGGGTTCCTG TTTGCCACAC TTGTGGTGAA CATGTTGGGT TGAATGTTAA  240
TGGTGAACCT TTTGTGGCTT GCCATGAATG TAATTTCCCT ATTTGTAAGA GTTGTTTTGA  300
GTATGATCTT AAGGAAGGAC GAAAAGCTTG CTTGCGTTGT GGTAGTCCAT ATGATGAAAA  360
CCTGTTGGAC GATGTCGAGA AGGCCACCGG CGATCAATCG ACAATGGCTG CACATTTGAA  420
CAAGTCTCAG GATGTTGGAA TTCATGCAAG ACATATCAGC AGTGTGTCTA CATTGGATAG  480
TGAAATGGCT GAAGACAATG GGAATTCGAT TTGGAAGAAC AGGGTGGAAA GTTGGAAAGA  540
AAAGAAGAAC AAGAAGAAGA AGCCTGCAAC AACTAAGGTT GAAAGAGAGG CTGAAATCCC  600
ACCTGAGCAA CAAATGGAAG ATAAACCGGC ACCGGATGCT TCCCAGCCCC TCTCGACTAT  660
AATTCCAATC CCGAAAAGCA GACTTGCACC ATACCGAACC GTGATCATTA TGCGATTGAT  720
CATTCTTGGT CTTTTCTTCC ATTATCGAGT AACAAACCCC GTTGACAGTG CTTTTGGACT  780
GTGGCTCACT TCAGTCATAT GTGAAATCTG GTTTGCATTT TCCTGGGTGT TGGATCAGTT  840
CCCTAAGTGG TATCCTGTTA ACAGGGAAAC ATACATTGAC AGACTATCTG CAAGATATGA  900
AAGAGAAGGT GAACCTGATG AACTTGCTGC AGTTGACTTC TTCGTGAGTA CAGTGGATCC  960
ATTGAAAGAG CCTCCATTGA TTACTGCCAA TACTGTGCTT TCCATCCTTG CCTTGGACTA 1020
```

Figure 6A

```
CCCGGTGGAT AAGGTCTCTT GTTATATATC TGATGATGGT GCGGCCATGC TGACATTTGA 1080
ATCTCTAGTA GAAACAGCCG ACTTTGCAAG AAAGTGGGTT CCATTCTGCA AAAAATTTTC 1140
CATTGAACCC CGGGCACCTG AGTTTTACTT CTCACAGAAG ATTGATTACT TGAAAGATAA 1200
AGTGCAGCCC TCTTTTGTAA AAGAACGTAG AGCTATGAAA AGAGATTATG AAGAGTACAA 1260
AATTCGAATC AATGCTTTAG TTGCAAAGGC TCAGAAAACA CCTGATGAAG GATGGACAAT 1320
GCAAGATGGA ACTTCTTGGC CAGGAAATAA CCCGCGTGAT CACCCTGGCA TGATTCAGGT 1380
TTTCCTTGGA TATAGTGGTG CTCGTGACAT CGAAGGAAAT GAACTTCCTC GACTGGTTTA 1440
CGTCTCTAGA GAGAAGAGAC CTGGCTACCA ACACCACAAA AAGGCTGGTG CTGAAAATGC 1500
TTTGGTTAGG GTGTCTGCAG TTCTTACAAA TGCTCCCTTC ATCCTCAATC TTGATTGTGA 1560
CCACTATGTT AACAATAGCA AGGCAGTTAG GGAGGCAATG TGCTTCTTGA TGGACCCACA 1620
AGTTGGTCGA GATGTATGCT ATGTGCAGTT TCCTCAAAGA TTTGATGGCA TAGATAGGAG 1680
TGATCGATAT GCCAATAGGA ACACAGTTTT CTTTGATGTT AACATGAAAG GTCTTGATGG 1740
AATCCAAGGG CCAGTTTATG TGGGAACAGG TTGTGTTTTC AATAGGCAAG CACTTTATGG 1800
CTATGGTCCA CCTTCAATGC CAAGTTTTCC CAAGTCATCC TCCTCATCTT GCTCGTGTTG 1860
CTGCCCGGGC AAGAAGGAAC CTAAAGATCC ATCAGAGCTT TATAGGGATG CAAAACGGGA 1920
AGAACTTGAT GCTGCCATCT TTAACCTTAG GGAAATTGAC AATTATGATG AGTATGAAAG 1980
ATCAATGTTG ATCTCTCAAA CAAGCTTTGA GAAAACTTTT GGCTTATCTT CAGTCTTCAT 2040
```

Figure 6B

```
TGAATCTACA CTAATGGAGA ATGGAGGAGT GGCTGAATCT GCCAACCCTT CCACACTAAT 2100
CAAGGAAGCA ATTCATGTCA TCAGCTGTGG CTATGAAGAG AAGACTGCAT GGGGGAAAGA 2160
GATTGGATGG ATATATGGTT CAGTCACTGA GGATATCTTA ACCGGCTTCA AAATGCACTG 2220
CCGAGGATGG AGATCGATTT ACTGCATGCC CTTAAGGCCA GCATTCAAAG GATCTGCACC 2280
CATCAATCTG TCTGATCGGT TGCACCAGGT TCTTCGATGG GCTCTTGGAT CTGTTGAAAT 2340
TTTCCTAAGC AGGCATTGCC CTCTATGGTA TGGCTTTGGA GGTGGTCGTC TTAAATGGCT 2400
TCAAAGACTA GCATATATAA ACACCATTGT CTATCCTTTC ACATCCCTTC CACTCATTGC 2460
CTATTGTTCA CTACCAGCAA TCTGTCTTCT CACAGGAAAA TTTATCATAC CAACGCTCTC 2520
AAACCTGGCA AGTGTTCTCT TTCTTGGCCT TTTCCTTTCC ATTATCGTGA CTGCTGTTCT 2580
CGAGCTCCGA TGGAGTGGTG TCAGCATTGA GGACTTATGG CGTAACGAGC AGTTTTGGGT 2640
CATCGGTGGC GTTTCAGCCC ATCTCTTTGC CGTCTTCCAA GGTTTCCTTA AGATGCTTGC 2700
GGGCATTGAC ACCAACTTTA CTGTCACTGC CAAAGCAGCT GATGATGCAG ATTTTGGTGA 2760
GCTCTACATT GTGAAATGGA CTACACTTCT AATCCCTCCA ACAACACTCC TCATCGTCAA 2820
CATGGTTGGT GTCGTTGCCG GATTCTCCGA TGCCCTCAAC AAAGGGTACG AAGCTTGGGG 2880
ACCACTCTTT GGCAAAGTGT TCTTTTCCTT CTGGGTCATC CTCCATCTTT ATCCATTCCT 2940
CAAAGGTCTT ATGGGACGCC AAAACAGGAC ACCAACCATT GTTGTCCTTT GGTCAGTGTT 3000
GTTGGCTTCT GTCTTCTCTC TTGTTTGGGT TCGGATCAAC CCGTTTGTCA GCACCGCCGA 3060
TAGCACCACC GTGTCACAGA GCTGCATTTC CATTGATTGT TGATGATATT ATGTGTTTCT 3120
```

Figure 6C

```
TAGAATTGAA ATCATTGCAA GTAAGTGGAC TGAAACATGT CTATTGACTA AGTTTTGAAC 3180
AGTTTGTACC CATTTTATTC TTAGCAGTGT GTAATTTTCC TAAACAATGC TATGAACTAT 3240
ACATATTTCA TTGATATTTA CATTAAATGA AACTACATCA GTCTGCAGAA AAAAAAAAAA 3300
AAAAAAAAAC TCGAGGGGGG GCCCGGTA                                    3328
```

Figure 6D

```
AACTAGTGGA TCCCCCGGGC TGCAGGAATT CGGCACGAGC GAGGAGATGG GTTCCGTTTT   60
GTAAGAAGCA TTGATCACCT AGGGGGCCCG ACGTCCTTAA GCCGTGCTCG CTCCTCTACC  120
CAAGGCAAAA CATTCTTCGT TAATGTTGAG CCCAGGGCGC CGGAGTTTTA TTTCAATGAG  180
AAGATTGATT ATTTGAAGGA CAAGGTCCAT ATTACAACTC GGGTCCCGCG GCCTCAAAAT  240
AAAGTTACTC TTCTAACTAA TAAACTTCCT GTTCCAGGTA CCTAGCTTTG TTAAAGAACG  300
GAGAGCCATG AAAAGGGAAT ATGAAGAATT TAAAGTAAGG ATCAATGCAT GGATCGAAAC  360
AATTTCTTGC CTCTCGGTAC TTTTCCCTTA TACTTCTTAA ATTTCATTCC TAGTTACGTA  420
TAGTAGCAAA AGCTCAGAAG AAACCAGAAG AAGGATGGGT GATGCAAGAT GGCACCCCAT  480
GGCCCGGAAA ATCATCGTTT TCGAGTCTTC TTTGGTCTTC TTCCTACCCA CTACGTTCTA  540
CCGTGGGGTA CCGGGCCTTT TAACACTCGT GATCATCCTG GAATGATTCA GGTCTATCTA  600
GGAAGTGCCG GTGCACTCGA TGTGGATGGC ATTGTGAGCA CTAGTAGGAC CTTACTAAGT  660
CCAGATAGAT CCTTCACGGC CACGTGAGCT ACACCTACCG AAAGAGCTGC CTCGACTTGT  720
CTATGTTTCT CGTGAGAAAC GACCTGGTTA TCAGCACCAT AAGAAAGCCG TTTCTCGACG  780
GAGCTGAACA GATACAAAGA GCACTCTTTG CTGGACCAAT AGTCGTGGTA TTCTTTCGGC  840
GTGCTGAGAA TGCTCTGGTT CGAGTTTCTG CAGTGCTTAC TAATGCACCC TTCATATTGA  900
ATCTGGATTG CACGACTCTT ACGAGACCAA GCTCAAAGAC GTCACGAATG ATTACGTGGG  960
AAGTATAACT TAGACCTAAC TGATCATTAC ATCAACAATA GCAAGGCCAT GAGGGAAGCG 1020
ATGTGCTTTT TAATGGATCC TCAGTTTGGA ACTAGTAATG TAGTTGTTAT CGTTCCGGTA 1080
```

Figure 7A

```
CTCCCTTCGC TACACGAAAA ATTACCTAGG AGTCAAACCT AAGAAGCTTT GTTATGTTCA  1140
ATTTCCACAG AGATTTGATG GTATTGATCG TCATGATCGA TATGCTAATC TTCTTCGAAA  1200
CAATACAAGT TAAAGGTGTC TCTAAACTAC CATAACTAGC AGTACTAGCT ATACGATTAG  1260
GAAATGTTGT CTTCTTTGAT ATCAACATGT TGGGATTAGA TGGACTTCAA GGCCCTGTAT  1320
ATGTAGGCAC CTTTACAACA GAAGAAACTA TAGTTGTACA ACCCTAATCT ACCTGAAGTT  1380
CCGGGACATA TACATCCGTG AGGGTGTGTT TTCAACAGGC AGGCATTGTA TGGCTACGAT  1440
CCACCAGTCT CTGAGAAACG ACCAAAGATG TCCCACACAA AAGTTGTCCG TCCGTAACAT  1500
ACCGATGCTA GGTGGTCAGA GACTCTTTGC TGGTTTCTAC ACATGTGATT GCTGGCCTTC  1560
TTGGTGTTGC TGTTGTTGCG GAGGTTCTAG GAAGAAATCA AAGAAGAAAG TGTACACTAA  1620
CGACCGGAAG AACCACAACG ACAACAACGC CTCCAAGATC CTTCTTTAGT TTCTTCTTTC  1680
GTGAAAAGAA GGGCTTACTC GGAGGTCTTT TATACGGAAA AAAGAAGAAG ATGATGGGCA  1740
AAAACTATGT CACTTTTCTT CCCGAATGAG CCTCCAGAAA ATATGCCTTT TTTCTTCTTC  1800
TACTACCCGT TTTTGATACA GAAAAAAGGG TCTGCACCAG TCTTTGATCT CGAAGAAATC  1860
GAAGAAGGGC TTGAAGGATA CGAAGAATTG CTTTTTTCCC AGACGTGGTC AGAAACTAGA  1920
GCTTCTTTAG CTTCTTCCCG AACTTCCTAT GCTTCTTAAC GAGAAATCGA CATTAATGTC  1980
GCAGAAGAAT TTCGAGAAAC GATTCGGACA ATCACCGGTT TTCATTGCCT CTCTTTAGCT  2040
GTAATTACAG CGTCTTCTTA AAGCTCTTTG CTAAGCCTGT TAGTGGCCAA AAGTAACGGA  2100
```

Figure 7B

```
CAACTTTGAT GGAAAATGGT GGCCTTCCTG AAGGAACTAA TTCCACATCA CTGATTAAAG  2160
AGGCCATTCA GTTGAAACTA CCTTTTACCA CCGGAAGGAC TTCCTTGATT AAGGTGTAGT  2220
GACTAATTTC TCCGGTAAGT CGTAATTAGC TGTGGTTATG AAGAAAAAAC TGAGTGGGGC  2280
AAAGAGATCG GATGGATTTA TGGGTCGGTG GCATTAATCG ACACCAATAC TTCTTTTTTG  2340
ACTCACCCCG TTTCTCTAGC CTACCTAAAT ACCCAGCCAC ACGGAAGATA TATTAACAGG  2400
TTTCAAGATG CATTGTAGAG GGTGGAAATC GGTTTATTGT GTACCGAAAA TGCCTTCTAT  2460
ATAATTGTCC AAAGTTCTAC GTAACATCTC CCACCTTTAG CCAAATAACA CATGGCTTTT  2520
GACCGGCATT CAAAGGGTCC GCTCCAATCA ATCTCTCGGA TCGGTTGCAC CAAGTTTTGA  2580
GATGGGCACT CTGGCCGTAA GTTTCCCAGG CGAGGTTAGT TAGAGAGCCT AGCCAACGTG  2640
GTTCAAAACT CTACCCGTGA TGGTTCTGTA GAAATTTTCC TTAGTCGTCA CTGTCCACTT  2700
TGGTATGGTT ATGGTGGAAA ACTGAAATGG ACCAAGACAT CTTTAAAAGG AATCAGCAGT  2760
GACAGGTGAA ACCATACCAA TACCACCTTT TGACTTTACC CTCGAGAGGC TTGCTTATAT  2820
CAACACCATT GTTTACCCTT TCACCTCGAT CCCTTTACTC GCCTATTGTA GAGCTCTCCG  2880
AACGAATATA GTTGTGGTAA CAAATGGGAA AGTGGAGCTA GGGAAATGAG CGGATAACAT  2940
CTATTCCAGC TGTTTGTCTT CTCACCGGCA AATTCATCAT TCCAACTCTA AGCAACCTTA  3000
CAAGTGTGTG GATAAGGTCG ACAAACAGAA GAGTGGCCGT TTAAGTAGTA AGGTTGAGAT  3060
TCGTTGGAAT GTTCACACAC GTTCTTGGCA CTTTTCCTCT CCATCATTGC AACTGGAGTG  3120
CTTGAACTTC GATGGAGCGG GGTTAGCATC CAAGAACCGT GAAAAGGAGA GGTAGTAACG  3180
```

Figure 7C

```
TTGACCTCAC GAACTTGAAG CTACCTCGCC CCAATCGTAG CAAGACTGGT GGCGCAATGA  3240
ACAATTCTGG GTGATCGGAG GTGTCTCCGC CCATCTTTTT GCTGTCTTCC GTTCTGACCA  3300
CCGCGTTACT TGTTAAGACC CACTAGCCTC CACAGAGGCG GGTAGAAAAA CGACAGAAGG  3360
AGGGCCTCCT CAAAGTCCTA GCTGGAGTAG ACACCAACTT CACCGTAACA GCAAAAGCAG  3420
CAGACGATAC TCCCGGAGGA GTTTCAGGAT CGACCTCATC TGTGGTTGAA GTGGCATTGT  3480
CGTTTTCGTC GTCTGCTATG AGAATTCGGT GAACTTTATC TCTTCAAATG GACAACTCTC  3540
TTAATCCCTC CCACAACTCT GATAATACTG TCTTAAGCCA CTTGAAATAG AGAAGTTTAC  3600
CTGTTGAGAG AATTAGGGAG GGTGTTGAGA CTATTATGAC AACATGGTCG GAGTCGTGGC  3660
CGGAGTTTCA GACGCAATCA ACAACGGCTA TGGTTCATGG GGTCCATTGT TTGTACCAGC  3720
CTCAGCACCG GCCTCAAAGT CTGCGTTAGT TGTTGCCGAT ACCAAGTACC CCAGGTAACA  3780
TCGGCAAACT GTTCTTCGCA TTCTGGGTCA TTCTTCATCT TTACCCATTC CTCAAAGGTT  3840
TGATGGGGAG AGCCGTTTGA CAAGAAGCGT AAGACCCAGT AAGAAGTAGA AATGGGTAAG  3900
GAGTTTCCAA ACTACCCCTC ACAAAACAGG ACGCCCACCA TTGTTGTGCT TTGGTCCATA  3960
CTTTTGGCAT CGATTTTCTC ACTGGTTTGG TGTTTTGTCC TGCGGGTGGT AACAACACGA  4020
AACCAGGTAT GAAAACCGTA GCTAAAAGAG TGACCAAACC GTACGGATCG ATCCCTTCTT  4080
GCCCAAACAA ACAGGTCCAG TTCTTAAACA ATGTGGCGTG GAGTGCTAAA CATGCCTAGC  4140
TAGGGAAGAA CGGGTTTGTT TGTCCAGGTC AAGAATTTGT TACACCGCAC CTCACGATTT  4200
```

Figure 7D

```
TGGTGTTTTA CAAACCTTTC TTATTATTTT ATTTTCCCTT TTTGCCACTA CTGTTGATTT  4260
GCTGTGATTC ACCACAAAAT GTTTGGAAAG AATAATAAAA TAAAAGGGAA AAACGGTGAT  4320
GACAACTAAA CGACACTAAG TAAAAGGGAT TTATCTTGTT TGTAAAAAGT CTCCTATGAT  4380
TTTGTTGGTT CAATTTAATT TCTATATGGT ATTTTCCCTA AATAGAACAA ACATTTTTCA  4440
GAGGATACTA AAACAACCAA GTTAAATTAA AGATATACCA AAAAAAATAT TTCTTTAAAT  4500
TAACTATAAA AAAAAAAAAA AAAAACTCGA GGGGGGGCCC GGTACCTTTT TTTATAAAGA  4560
AATTTAATTG ATATTTTTTT TTTTTTTTTT TGAGCTCCCC CCCGGGCCAT GG          4612
```

Figure 7E

```
GGGTGATTGA CTAAAATTTT TAAAAATTTT GAAGGTTTTA ATGAGAATTT TTAAACAATT   60
TTGTATGTTA AACTAAAACT TTCAAAAAAA ATTTTGAAAG GTTTAATGAG AATTTTAAAA  120
ATTTTGAGCG GGCTAATTAA AATTTTTAAA AAATGTATAA TAAAAAAATT CAAAAACTCT  180
TTGAGGCCAT AAAGGTCATC GGGCCCTTAA ATACATCAGC TTGTTGTTTC CTCATATTAC  240
TCATGTTATT TCAGTTAACA GATATAATGG CTATCATTTG ATTTAGGAGT GAAATCTAAA  300
AATTCGAAAA GTATAAAAAC TAAAAAGGAT TAAATTGAAG AACATTAATT AAATCAACAA  360
TTTACTATTC CAATAACAGA ATTTTGAGTT AACAAATTTA ACTGCTACAA TTTGGTTCGA  420
GACCAAAATT ACAAAACCCG AAAAGTATTG GGACTAAAAT TGATCAAATT AGAGTACATG  480
GGTTAAATTC ACAACTTACT TATGGTACAA GGATTAATAG CATAATTTCT CCTTAGGCAA  540
ATGCCAGTTA GTTAAAGATG TACCTTGCCC AACCGAAAGC TTCCTTAAAC TTCCCGCAAT  600
TTTTTAAATT TCTTTTTCCC TTAGAAAAAA GAACAAAAAT GTAAGCTTTG CTTGTCAGAG  660
ATTTCTCTGC AAATACATTG ACACCAACAA CCTACCCTCC ATTACACTAC CAACCGGCCT  720
TCCCCTTCAA CTTTTCTTCA CCATTACAAC ATGCCTATCT CCACCCTTAG CCCAACATGC  780
ACTTATATCT TGTGTTTGGT TGTTTTTCTT TTTCATATAA AAACACACAC CAAGACACAA  840
AGGTATTGAG AGGTAAGTAG AGGGAAAGAC CCTTTGGTTA GCATATTGTT TGTAGCATTG  900
GGTTTTTTCT CAAGGAAGAA GAAGGAGAAA GATAAGTACT TTTTTTGAGA ATGATGGAAT  960
CTGGGGTTCC TGTTTGCCAC ACTTGTGGTG AACATGTTGG GTTGAATGTA AGCCGAATTC 1020
CAGCACACTG GCGGCCGTTA CTAGTGGATC CGCGCTCGGT ACC                  1063
```

Figure 8

SEQUENCE LISTING

<160> NUMBER OF SEQ ID NOS: 12

<210> SEQ ID NO: 1
<211> LENGTH: 3328
<212> TYPE: DNA
<213> ORGANISM: Artificial Sequence
<220> FEATURE:
<223> OTHER INFORMATION: Synthetic Oligonucleotide

<400> SEQUENCE: 1

```
cgaaattaac cctcactaaa gggaacaaaa gctggagctc caccgcggtg gcggccgctc     60
tagaactagt ggatcccccg ggctgcagga attcggcacg agggttagca tattgtttgt    120
agcattgggt ttttttctca aggaagaaga aggagaaaga taagtacttt ttttgagaat    180
gatggaatct ggggttcctg tttgccacac ttgtggtgaa catgttgggt tgaatgttaa    240
tggtgaacct tttgtggctt gccatgaatg taatttccct atttgtaaga gttgttttga    300
gtatgatctt aaggaaggac gaaaagcttg cttgcgttgt ggtagtccat atgatgaaaa    360
cctgttggac gatgtcgaga aggccaccgg cgatcaatcg acaatggctg cacatttgaa    420
caagtctcag gatgttggaa ttcatgcaag acatatcagc agtgtgtcta cattggatag    480
tgaaatggct gaagacaatg ggaattcgat ttggaagaac agggtggaaa gttggaaaga    540
aaagaagaac aagaagaaga agcctgcaac aactaaggtt gaaagagagg ctgaaatccc    600
acctgagcaa caaatggaag ataaaccggc accggatgct tcccagcccc tctcgactat    660
aattccaatc ccgaaaagca gacttgcacc ataccgaacc gtgatcatta tgcgattgat    720
cattcttggt cttttcttcc attatcgagt aacaaacccc gttgacagtg cttttggact    780
gtggctcact tcagtcatat gtgaaatctg gtttgcattt tcctgggtgt tggatcagtt    840
ccctaagtgg tatcctgtta acagggaaac atacattgac agactatctg caagatatga    900
aagagaaggt gaacctgatg aacttgctgc agttgacttc ttcgtgagta cagtggatcc    960
attgaaagag cctccattga ttactgccaa tactgtgctt tccatccttg ccttggacta   1020
cccggtggat aaggtctctt gttatatatc tgatgatggt gcggccatgc tgacatttga   1080
atctctagta gaaacagccg actttgcaag aaagtgggtt ccattctgca aaaaattttc   1140
cattgaaccc cgggcacctg agttttactt ctcacagaag attgattact tgaaagataa   1200
agtgcagccc tcttttgtaa aagaacgtag agctatgaaa agagattatg aagagtacaa   1260
aattcgaatc aatgctttag ttgcaaaggc tcagaaaaca cctgatgaag gatggacaat   1320
gcaagatgga acttcttggc caggaaataa cccgcgtgat caccctggca tgattcaggt   1380
tttccttgga tatagtggtg ctcgtgacat cgaaggaaat gaacttcctc gactggttta   1440
cgtctctaga gagaagagac ctggctacca acaccacaaa aaggctggtg ctgaaaatgc   1500
tttggttagg gtgtctgcag ttcttacaaa tgctcccttc atcctcaatc ttgattgtga   1560
ccactatgtt aacaatagca aggcagttag ggaggcaatg tgcttcttga tggacccaca   1620
agttggtcga gatgtatgct atgtgcagtt tcctcaaaga tttgatggca tagataggag   1680
tgatcgatat gccaatagga acacagtttt ctttgatgtt aacatgaaag gtcttgatgg   1740
aatccaaggg ccagtttatg tgggaacagg ttgtgttttc aataggcaag cactttatgg   1800
ctatggtcca ccttcaatgc caagttttcc caagtcatcc tcctcatctt gctcgtgttg   1860
ctgcccgggc aagaaggaac ctaaagatcc atcagagctt tatagggatg caaaacggga   1920
agaacttgat gctgccatct ttaaccttag ggaaattgac aattatgatg agtatgaaag   1980
```

```
atcaatgttg atctctcaaa caagctttga gaaaactttt ggcttatctt cagtcttcat   2040
tgaatctaca ctaatggaga atggaggagt ggctgaatct gccaaccctt ccacactaat   2100
caaggaagca attcatgtca tcagctgtgg ctatgaagag aagactgcat gggggaaaga   2160
gattggatgg atatatggtt cagtcactga ggatatctta accggcttca aaatgcactg   2220
ccgaggatgg agatcgattt actgcatgcc cttaaggcca gcattcaaag gatctgcacc   2280
catcaatctg tctgatcggt tgcaccaggt tcttcgatgg gctcttggat ctgttgaaat   2340
tttcctaagc aggcattgcc ctctatggta tggctttgga ggtggtcgtc ttaaatggct   2400
tcaaagacta gcatatataa acaccattgt ctatcctttc acatcccttc cactcattgc   2460
ctattgttca ctaccagcaa tctgtcttct cacaggaaaa tttatcatac caacgctctc   2520
aaacctggca agtgttctct ttcttggcct tttcctttcc attatcgtga ctgctgttct   2580
cgagctccga tggagtggtg tcagcattga ggacttatgg cgtaacgagc agttttgggt   2640
catcggtggc gtttcagccc atctctttgc cgtcttccaa ggtttcctta agatgcttgc   2700
gggcattgac accaacttta ctgtcactgc caaagcagct gatgatgcag attttggtga   2760
gctctacatt gtgaaatgga ctacacttct aatccctcca acaacactcc tcatcgtcaa   2820
catggttggt gtcgttgccg gattctccga tgccctcaac aaagggtacg aagcttgggg   2880
accactcttt ggcaaagtgt tcttttcctt ctgggtcatc ctccatcttt atccattcct   2940
caaaggtctt atgggacgcc aaaacaggac accaaccatt gttgtccttt ggtcagtgtt   3000
gttggcttct gtcttctctc ttgtttgggt tcggatcaac ccgtttgtca gcaccgccga   3060
tagcaccacc gtgtcacaga gctgcatttc cattgattgt tgatgatatt atgtgtttct   3120
tagaattgaa atcattgcaa gtaagtggac tgaaacatgt ctattgacta agttttgaac   3180
agtttgtacc cattttattc ttagcagtgt gtaattttcc taaacaatgc tatgaactat   3240
acatatttca ttgatattta cattaaatga aactacatca gtctgcagaa aaaaaaaaaa   3300
aaaaaaaaac tcgagggggg gcccggta                                      3328
```

<210> SEQ ID NO: 2
<211> LENGTH: 4612
<212> TYPE: DNA
<213> ORGANISM: Artificial Sequence
<220> FEATURE:
<223> OTHER INFORMATION: Synthetic Oligonucleotide

<400> SEQUENCE: 2

```
aactagtgga tcccccgggc tgcaggaatt cggcacgagc gaggagatgg gttccgtttt     60
gtaagaagca ttgatcacct agggggcccg acgtccttaa gccgtgctcg ctcctctacc    120
caaggcaaaa cattcttcgt taatgttgag cccagggcgc cggagtttta tttcaatgag    180
aagattgatt atttgaagga caaggtccat attacaactc gggtcccgcg gcctcaaaat    240
aaagttactc ttctaactaa taaacttcct gttccaggta cctagctttg ttaaagaacg    300
gagagccatg aaaagggaat atgaagaatt taaagtaagg atcaatgcat ggatcgaaac    360
aatttcttgc ctctcggtac ttttccctta tacttcttaa atttcattcc tagttacgta    420
tagtagcaaa agctcagaag aaaccagaag aaggatgggt gatgcaagat ggcaccccat    480
ggcccggaaa atcatcgttt tcgagtcttc tttggtcttc ttcctaccca ctacgttcta    540
ccgtggggta ccgggccttt taacactcgt gatcatcctg gaatgattca ggtctatcta    600
ggaagtgccg gtgcactcga tgtggatggc attgtgagca ctagtaggac cttactaagt    660
```

-continued

```
ccagatagat ccttcacggc cacgtgagct acacctaccg aaagagctgc ctcgacttgt    720
ctatgtttct cgtgagaaac gacctggtta tcagcaccat aagaaagccg tttctcgacg    780
gagctgaaca gatacaaaga gcactctttg ctggaccaat agtcgtggta ttctttcggc    840
gtgctgagaa tgctctggtt cgagtttctg cagtgcttac taatgcaccc ttcatattga    900
atctggattg cacgactctt acgagaccaa gctcaaagac gtcacgaatg attacgtggg    960
aagtataact tagacctaac tgatcattac atcaacaata gcaaggccat gagggaagcg   1020
atgtgctttt taatggatcc tcagtttgga actagtaatg tagttgttat cgttccggta   1080
ctcccttcgc tacacgaaaa attacctagg agtcaaacct aagaagcttt gttatgttca   1140
atttccacag agatttgatg gtattgatcg tcatgatcga tatgctaatc ttcttcgaaa   1200
caatacaagt taaaggtgtc tctaaactac cataactagc agtactagct atacgattag   1260
gaaatgttgt cttctttgat atcaacatgt tgggattaga tggacttcaa ggccctgtat   1320
atgtaggcac ctttacaaca gaagaaacta tagttgtaca accctaatct acctgaagtt   1380
ccgggacata tacatccgtg agggtgtgtt ttcaacaggc aggcattgta tggctacgat   1440
ccaccagtct ctgagaaacg accaaagatg tcccacacaa aagttgtccg tccgtaacat   1500
accgatgcta ggtggtcaga gactctttgc tggtttctac acatgtgatt gctggccttc   1560
ttggtgttgc tgttgttgcg gaggttctag gaagaaatca aagaagaaag tgtacactaa   1620
cgaccggaag aaccacaacg acaacaacgc ctccaagatc cttctttagt ttcttctttc   1680
gtgaaaagaa gggcttactc ggaggtcttt tatacggaaa aaagaagaag atgatgggca   1740
aaaactatgt cacttttctt cccgaatgag cctccagaaa atatgccttt tttcttcttc   1800
tactacccgt tttgatacca gaaaaaaggg tctgcaccag tctttgatct cgaagaaatc   1860
gaagaagggc ttgaaggata cgaagaattg ctttttttccc agacgtggtc agaaactaga   1920
gcttctttag cttcttcccg aacttcctat gcttcttaac gagaaatcga cattaatgtc   1980
gcagaagaat ttcgagaaac gattcggaca atcaccggtt ttcattgcct ctctttagct   2040
gtaattacag cgtcttctta aagctctttg ctaagcctgt tagtggccaa aagtaacgga   2100
caactttgat ggaaaatggt ggccttcctg aaggaactaa ttccacatca ctgattaaag   2160
aggccattca gttgaaacta ccttttacca ccggaaggac ttccttgatt aaggtgtagt   2220
gactaatttc tccggtaagt cgtaattagc tgtggttatg aagaaaaaac tgagtggggc   2280
aaagagatcg gatggattta tgggtcggtg gcattaatcg acaccaatac ttctttttttg   2340
actcaccccg tttctctagc ctacctaaat acccagccac acggaagata tattaacagg   2400
tttcaagatg cattgtagag ggtggaaatc ggtttattgt gtaccgaaaa tgccttctat   2460
ataattgtcc aaagttctac gtaacatctc ccacctttag ccaaataaca catggctttt   2520
gaccggcatt caaagggtcc gctccaatca atctctcgga tcggttgcac caagttttga   2580
gatgggcact ctggccgtaa gtttcccagg cgaggttagt tagagagcct agccaacgtg   2640
gttcaaaact ctacccgtga tggttctgta gaaattttcc ttagtcgtca ctgtccactt   2700
tggtatggtt atggtggaaa actgaaatgg accaagacat ctttaaaagg aatcagcagt   2760
gacaggtgaa accataccaa taccaccttt tgactttacc ctcgagaggc ttgcttatat   2820
caacaccatt gtttaccctt tcacctcgat ccctttactc gcctattgta gagctctccg   2880
aacgaatata gttgtggtaa caaatgggaa agtggagcta gggaaatgag cggataacat   2940
ctattccagc tgtttgtctt ctcaccggca aattcatcat tccaactcta agcaacctta   3000
caagtgtgtg gataaggtcg acaaacagaa gagtggccgt ttaagtagta aggttgagat   3060
```

-continued

```
tcgttggaat gttcacacac gttcttggca cttttcctct ccatcattgc aactggagtg   3120

cttgaacttc gatggagcgg ggttagcatc caagaaccgt gaaaaggaga ggtagtaacg   3180

ttgacctcac gaacttgaag ctacctcgcc ccaatcgtag caagactggt ggcgcaatga   3240

acaattctgg gtgatcggag gtgtctccgc ccatcttttt gctgtcttcc gttctgacca   3300

ccgcgttact tgttaagacc cactagcctc cacagaggcg ggtagaaaaa cgacagaagg   3360

agggcctcct caaagtccta gctggagtag acaccaactt caccgtaaca gcaaaagcag   3420

cagacgatac tcccggagga gtttcaggat cgacctcatc tgtggttgaa gtggcattgt   3480

cgttttcgtc gtctgctatg agaattcggt gaactttatc tcttcaaatg gacaactctc   3540

ttaatccctc ccacaactct gataatactg tcttaagcca cttgaaatag agaagtttac   3600

ctgttgagag aattagggag ggtgttgaga ctattatgac aacatggtcg gagtcgtggc   3660

cggagtttca gacgcaatca acaacggcta tggttcatgg ggtccattgt ttgtaccagc   3720

ctcagcaccg gcctcaaagt ctgcgttagt tgttgccgat accaagtacc ccaggtaaca   3780

tcggcaaact gttcttcgca ttctgggtca ttcttcatct ttacccattc ctcaaaggtt   3840

tgatggggag agccgtttga caagaagcgt aagacccagt aagaagtaga aatgggtaag   3900

gagtttccaa actacccctc acaaaacagg acgcccacca ttgttgtgct ttggtccata   3960

cttttggcat cgattttctc actggtttgg tgttttgtcc tgcgggtggt aacaacacga   4020

aaccaggtat gaaaaccgta gctaaaagag tgaccaaacc gtacggatcg atcccttctt   4080

gcccaaacaa acaggtccag ttcttaaaca atgtggcgtg gagtgctaaa catgcctagc   4140

tagggaagaa cgggtttgtt tgtccaggtc aagaatttgt tacaccgcac ctcacgattt   4200

tggtgtttta caaacctttc ttattatttt attttccctt tttgccacta ctgttgattt   4260

gctgtgattc accacaaaat gtttggaaag aataataaaa taaaagggaa aaacggtgat   4320

gacaactaaa cgacactaag taaaagggat ttatcttgtt tgtaaaaagt ctcctatgat   4380

tttgttggtt caatttaatt tctatatggt attttcccta aatagaacaa acatttttca   4440

gaggatacta aaacaaccaa gttaaattaa agatatacca aaaaaaatat ttctttaaat   4500

taactataaa aaaaaaaaaa aaaaactcga ggggggcccc ggtacctttt tttataaaga   4560

aatttaattg atattttttt tttttttttt tgagctcccc cccgggccat gg           4612
```

<210> SEQ ID NO: 3
<211> LENGTH: 1063
<212> TYPE: DNA
<213> ORGANISM: Artificial Sequence
<220> FEATURE:
<223> OTHER INFORMATION: Synthetic Oligonucleotide

<400> SEQUENCE: 3

```
gggtgattga ctaaaatttt taaaaatttt gaaggtttta atgagaattt ttaaacaatt     60

ttgtatgtta aactaaaact ttcaaaaaaa attttgaaag gtttaatgag aattttaaaa    120

attttgagcg ggctaattaa aatttttaaa aaatgtataa taaaaaaatt caaaaactct    180

ttgaggccat aaaggtcatc gggcccttaa atacatcagc ttgttgtttc ctcatattac    240

tcatgttatt tcagttaaca gatataatgg ctatcatttg atttaggagt gaaatctaaa    300

aattcgaaaa gtataaaaac taaaaaggat taaattgaag aacattaatt aaatcaacaa    360

tttactattc caataacaga attttgagtt aacaaattta actgctacaa tttggttcga    420

gaccaaaatt acaaaacccg aaaagtattg ggactaaaat tgatcaaatt agagtacatg    480
```

-continued

```
ggttaaattc acaacttact tatggtacaa ggattaatag cataatttct ccttaggcaa    540

atgccagtta gttaaagatg taccttgccc aaccgaaagc ttccttaaac ttcccgcaat    600

tttttaaatt tctttttccc ttagaaaaaa gaacaaaaat gtaagctttg cttgtcagag    660

atttctctgc aaatacattg acaccaacaa cctaccctcc attacactac caaccggcct    720

tccccttcaa cttttcttca ccattacaac atgcctatct ccacccttag cccaacatgc    780

acttatatct tgtgtttggt tgtttttctt tttcatataa aaacacacac caagacacaa    840

aggtattgag aggtaagtag agggaaagac cctttggtta gcatattgtt tgtagcattg    900

ggtttttctt caaggaagaa gaaggagaaa gataagtact tttttgaga atgatggaat    960

ctggggttcc tgtttgccac acttgtggtg aacatgttgg gttgaatgta agccgaattc   1020

cagcacactg gcggccgtta ctagtggatc cgcgctcggt acc                     1063


<210> SEQ ID NO: 4
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 4

attgaattcc tgggtgttgg atcagtt                                         27


<210> SEQ ID NO: 5
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 5

attctcgagt ggaagggatt gaaa                                            24


<210> SEQ ID NO: 6
<211> LENGTH: 974
<212> TYPE: PRT
<213> ORGANISM: Gossypim hirsutum

<400> SEQUENCE: 6

Met Met Glu Ser Gly Val Pro Val Cys His Thr Cys Gly Glu His Val
 1               5                  10                  15

Gly Leu Asn Val Asn Gly Glu Pro Phe Val Ala Cys His Glu Cys Asn
            20                  25                  30

Phe Pro Ile Cys Lys Ser Cys Phe Glu Tyr Asp Leu Lys Glu Gly Arg
        35                  40                  45

Lys Ala Cys Leu Arg Cys Gly Ser Pro Tyr Asp Glu Asn Leu Leu Asp
    50                  55                  60

Asp Val Glu Lys Ala Thr Gly Asp Gln Ser Thr Met Ala Ala His Leu
65                  70                  75                  80

Asn Lys Ser Gln Asp Val Gly Ile His Ala Arg His Ile Ser Ser Val
                85                  90                  95

Ser Thr Leu Asp Ser Glu Met Ala Glu Asp Asn Gly Asn Ser Ile Trp
            100                 105                 110

Lys Asn Arg Val Glu Ser Trp Lys Glu Lys Lys Asn Lys Lys Lys Lys
        115                 120                 125

Pro Ala Thr Thr Lys Val Glu Arg Glu Ala Glu Ile Pro Pro Glu Gln
    130                 135                 140
```

-continued

```
Gln Met Glu Asp Lys Pro Ala Pro Asp Ala Ser Gln Pro Leu Ser Thr
145                 150                 155                 160

Ile Ile Pro Ile Pro Lys Ser Arg Leu Ala Pro Tyr Arg Thr Val Ile
                165                 170                 175

Ile Met Arg Leu Ile Ile Leu Gly Leu Phe Phe His Tyr Arg Val Thr
            180                 185                 190

Asn Pro Val Asp Ser Ala Phe Gly Leu Trp Leu Thr Ser Val Ile Cys
        195                 200                 205

Glu Ile Trp Phe Ala Phe Ser Trp Val Leu Asp Gln Phe Pro Lys Trp
    210                 215                 220

Tyr Pro Val Asn Arg Glu Thr Tyr Ile Asp Arg Leu Ser Ala Arg Tyr
225                 230                 235                 240

Glu Arg Glu Gly Glu Pro Asp Glu Leu Ala Ala Val Asp Phe Phe Val
                245                 250                 255

Ser Thr Val Asp Pro Leu Lys Glu Pro Pro Leu Ile Thr Ala Asn Thr
            260                 265                 270

Val Leu Ser Ile Leu Ala Leu Asp Tyr Pro Val Asp Lys Val Ser Cys
        275                 280                 285

Tyr Ile Ser Asp Asp Gly Ala Ala Met Leu Thr Phe Glu Ser Leu Val
    290                 295                 300

Glu Thr Ala Asp Phe Ala Arg Lys Trp Val Pro Phe Cys Lys Lys Phe
305                 310                 315                 320

Ser Ile Glu Pro Arg Ala Pro Glu Phe Tyr Phe Ser Gln Lys Ile Asp
                325                 330                 335

Tyr Leu Lys Asp Lys Val Gln Pro Ser Phe Val Lys Glu Arg Arg Ala
            340                 345                 350

Met Lys Arg Asp Tyr Glu Glu Tyr Lys Ile Arg Ile Asn Ala Leu Val
        355                 360                 365

Ala Lys Ala Gln Lys Thr Pro Asp Glu Gly Trp Thr Met Gln Asp Gly
    370                 375                 380

Thr Ser Trp Pro Gly Asn Asn Pro Arg Asp His Pro Gly Met Ile Gln
385                 390                 395                 400

Val Phe Leu Gly Tyr Ser Gly Ala Arg Asp Ile Glu Gly Asn Glu Leu
                405                 410                 415

Pro Arg Leu Val Tyr Val Ser Arg Glu Lys Arg Pro Gly Tyr Gln His
            420                 425                 430

His Lys Lys Ala Gly Ala Glu Asn Ala Leu Val Arg Val Ser Ala Val
        435                 440                 445

Leu Thr Asn Ala Pro Phe Ile Leu Asn Leu Asp Cys Asp His Tyr Val
    450                 455                 460

Asn Asn Ser Lys Ala Val Arg Glu Ala Met Cys Phe Leu Met Asp Pro
465                 470                 475                 480

Gln Val Gly Arg Asp Val Cys Tyr Val Gln Phe Pro Gln Arg Phe Asp
                485                 490                 495

Gly Ile Asp Arg Ser Asp Arg Tyr Ala Asn Arg Asn Thr Val Phe Phe
            500                 505                 510

Asp Val Asn Met Lys Gly Leu Asp Gly Ile Gln Gly Pro Val Tyr Val
        515                 520                 525

Gly Thr Gly Cys Val Phe Asn Arg Gln Ala Leu Tyr Gly Tyr Gly Pro
    530                 535                 540

Pro Ser Met Pro Ser Phe Pro Lys Ser Ser Ser Ser Ser Cys Ser Cys
545                 550                 555                 560

Cys Cys Pro Gly Lys Lys Glu Pro Lys Asp Pro Ser Glu Leu Tyr Arg
```

-continued

```
                565                 570                 575

Asp Ala Lys Arg Glu Glu Leu Asp Ala Ala Ile Phe Asn Leu Arg Glu
            580                 585                 590

Ile Asp Asn Tyr Asp Glu Tyr Glu Arg Ser Met Leu Ile Ser Gln Thr
        595                 600                 605

Ser Phe Glu Lys Thr Phe Gly Leu Ser Ser Val Phe Ile Glu Ser Thr
    610                 615                 620

Leu Met Glu Asn Gly Gly Val Ala Glu Ser Ala Asn Pro Ser Thr Leu
625                 630                 635                 640

Ile Lys Glu Ala Ile His Val Ile Ser Cys Gly Tyr Glu Glu Lys Thr
                645                 650                 655

Ala Trp Gly Lys Glu Ile Gly Trp Ile Tyr Gly Ser Val Thr Glu Asp
            660                 665                 670

Ile Leu Thr Gly Phe Lys Met His Cys Arg Gly Trp Arg Ser Ile Tyr
        675                 680                 685

Cys Met Pro Leu Arg Pro Ala Phe Lys Gly Ser Ala Pro Ile Asn Leu
    690                 695                 700

Ser Asp Arg Leu His Gln Val Leu Arg Trp Ala Leu Gly Ser Val Glu
705                 710                 715                 720

Ile Phe Leu Ser Arg His Cys Pro Leu Trp Tyr Gly Phe Gly Gly Gly
                725                 730                 735

Arg Leu Lys Trp Leu Gln Arg Leu Ala Tyr Ile Asn Thr Ile Val Tyr
            740                 745                 750

Pro Phe Thr Ser Leu Pro Leu Ile Ala Tyr Cys Ser Leu Pro Ala Ile
        755                 760                 765

Cys Leu Leu Thr Gly Lys Phe Ile Ile Pro Thr Leu Ser Asn Leu Ala
    770                 775                 780

Ser Val Leu Phe Leu Gly Leu Phe Leu Ser Ile Ile Val Thr Ala Val
785                 790                 795                 800

Leu Glu Leu Arg Trp Ser Gly Val Ser Ile Glu Asp Leu Trp Arg Asn
                805                 810                 815

Glu Gln Phe Trp Val Ile Gly Gly Val Ser Ala His Leu Phe Ala Val
            820                 825                 830

Phe Gln Gly Phe Leu Lys Met Leu Ala Gly Ile Asp Thr Asn Phe Thr
        835                 840                 845

Val Thr Ala Lys Ala Ala Asp Asp Ala Asp Phe Gly Glu Leu Tyr Ile
    850                 855                 860

Val Lys Trp Thr Thr Leu Leu Ile Pro Pro Thr Thr Leu Leu Ile Val
865                 870                 875                 880

Asn Met Val Gly Val Val Ala Gly Phe Ser Asp Ala Leu Asn Lys Gly
                885                 890                 895

Tyr Glu Ala Trp Gly Pro Leu Phe Gly Lys Val Phe Phe Ser Phe Trp
            900                 905                 910

Val Ile Leu His Leu Tyr Pro Phe Leu Lys Gly Leu Met Gly Arg Gln
        915                 920                 925

Asn Arg Thr Pro Thr Ile Val Val Leu Trp Ser Val Leu Leu Ala Ser
    930                 935                 940

Val Phe Ser Leu Val Trp Val Arg Ile Asn Pro Phe Val Ser Thr Ala

945                 950                 955                 960
Asp Ser Thr Thr Val Ser Gln Ser Cys Ile Ser Ile Asp Cys
                965                 970


<210> SEQ ID NO: 7
```

-continued

```
<211> LENGTH: 685
<212> TYPE: PRT
<213> ORGANISM: Gossypium hirsutum

<400> SEQUENCE: 7

Ala Arg Arg Trp Val Pro Phe Cys Lys Lys His Asn Val Glu Pro Arg
 1               5                  10                  15

Ala Pro Glu Phe Tyr Phe Asn Glu Lys Ile Asp Tyr Leu Lys Asp Lys
            20                  25                  30

Val His Pro Ser Phe Val Lys Glu Arg Arg Ala Met Lys Arg Glu Tyr
        35                  40                  45

Glu Glu Phe Lys Val Arg Ile Asn Ala Leu Val Ala Lys Ala Gln Lys
    50                  55                  60

Lys Pro Glu Glu Gly Trp Val Met Gln Asp Gly Thr Pro Trp Pro Gly
65                  70                  75                  80

Asn Asn Thr Arg Asp His Pro Gly Met Ile Gln Val Tyr Leu Gly Ser
                85                  90                  95

Ala Gly Ala Leu Asp Val Asp Gly Lys Glu Leu Pro Arg Leu Val Tyr
            100                 105                 110

Val Ser Arg Glu Lys Arg Pro Gly Tyr Gln His His Lys Lys Ala Gly
        115                 120                 125

Ala Glu Asn Ala Leu Val Arg Val Ser Ala Val Leu Thr Asn Ala Pro
    130                 135                 140

Phe Ile Leu Asn Leu Asp Cys Asp His Tyr Ile Asn Asn Ser Lys Ala
145                 150                 155                 160

Met Arg Glu Ala Met Cys Phe Leu Met Asp Pro Gln Phe Gly Lys Lys
                165                 170                 175

Leu Cys Tyr Val Gln Phe Pro Gln Arg Phe Asp Gly Ile Asp Arg His
            180                 185                 190

Asp Arg Tyr Ala Asn Arg Asn Val Val Phe Phe Asp Ile Asn Met Leu
        195                 200                 205

Gly Leu Asp Gly Leu Gln Gly Pro Val Tyr Val Gly Thr Gly Cys Val
    210                 215                 220

Phe Asn Arg Gln Ala Leu Tyr Gly Tyr Asp Pro Pro Val Ser Glu Lys
225                 230                 235                 240

Arg Pro Lys Met Thr Cys Asp Cys Trp Pro Ser Trp Cys Cys Cys Cys
                245                 250                 255

Cys Gly Gly Ser Arg Lys Lys Ser Lys Lys Lys Gly Glu Lys Lys Gly
            260                 265                 270

Leu Leu Gly Gly Leu Leu Tyr Gly Lys Lys Lys Lys Met Met Gly Lys
        275                 280                 285

Asn Tyr Val Lys Lys Gly Ser Ala Pro Val Phe Asp Leu Glu Glu Ile
    290                 295                 300

Glu Glu Gly Leu Glu Gly Tyr Glu Glu Leu Glu Lys Ser Thr Leu Met
305                 310                 315                 320

Ser Gln Lys Asn Phe Glu Lys Arg Phe Gly Gln Ser Pro Val Phe Ile
                325                 330                 335

Ala Ser Thr Leu Met Glu Asn Gly Gly Leu Pro Glu Gly Thr Asn Ser
            340                 345                 350

Thr Ser Leu Ile Lys Glu Ala Ile His Val Ile Ser Cys Gly Tyr Glu
        355                 360                 365

Glu Lys Thr Glu Trp Gly Lys Glu Ile Gly Trp Ile Tyr Gly Ser Val
    370                 375                 380

Thr Glu Asp Ile Leu Thr Gly Phe Lys Met His Cys Arg Gly Trp Lys
```

-continued

```
385                 390                 395                 400

Ser Val Tyr Cys Val Pro Lys Arg Pro Ala Phe Lys Gly Ser Ala Pro
                405                 410                 415

Ile Asn Leu Ser Asp Arg Leu His Gln Val Leu Arg Trp Ala Leu Gly
            420                 425                 430

Ser Val Glu Ile Phe Leu Ser Arg His Cys Pro Leu Trp Tyr Gly Tyr
        435                 440                 445

Gly Gly Lys Leu Lys Trp Leu Glu Arg Leu Ala Tyr Ile Asn Thr Ile
    450                 455                 460

Val Tyr Pro Phe Thr Ser Ile Pro Leu Leu Ala Tyr Cys Thr Ile Pro
465                 470                 475                 480

Ala Val Cys Leu Leu Thr Gly Lys Phe Ile Ile Pro Thr Leu Ser Asn
                485                 490                 495

Leu Thr Ser Val Trp Phe Leu Ala Leu Phe Leu Ser Ile Ile Ala Thr
            500                 505                 510

Gly Val Leu Glu Leu Arg Trp Ser Gly Val Ser Ile Gln Asp Trp Trp
        515                 520                 525

Arg Asn Glu Gln Phe Trp Val Ile Gly Gly Val Ser Ala His Leu Phe
    530                 535                 540

Ala Val Phe Gln Gly Leu Leu Lys Val Leu Ala Gly Val Asp Thr Asn
545                 550                 555                 560

Phe Thr Val Thr Ala Lys Ala Ala Asp Asp Thr Glu Phe Gly Glu Leu
                565                 570                 575

Tyr Leu Phe Lys Trp Thr Thr Leu Leu Ile Pro Pro Thr Thr Leu Ile
            580                 585                 590

Ile Leu Asn Met Val Gly Val Val Ala Gly Val Ser Asp Ala Ile Asn
        595                 600                 605

Asn Gly Tyr Gly Ser Trp Gly Pro Leu Phe Gly Lys Leu Phe Phe Ala
    610                 615                 620

Phe Trp Val Ile Leu His Leu Tyr Pro Phe Leu Lys Gly Leu Met Gly
625                 630                 635                 640

Arg Gln Asn Arg Thr Pro Thr Ile Val Val Leu Trp Ser Ile Leu Leu
                645                 650                 655

Ala Ser Ile Phe Ser Leu Val Trp Val Arg Ile Asp Pro Phe Leu Pro
            660                 665                 670

Lys Gln Thr Gly Pro Val Leu Lys Gln Cys Gly Val Glu
        675                 680                 685


<210> SEQ ID NO: 8
<211> LENGTH: 881
<212> TYPE: PRT
<213> ORGANISM: Oryzae sativa

<400> SEQUENCE: 8

Gly Asn Val Ala Trp Lys Glu Arg Val Asp Gly Trp Lys Leu Lys Gln
 1               5                  10                  15

Asp Lys Gly Ala Ile Pro Met Thr Asn Gly Thr Ser Ile Ala Pro Ser
            20                  25                  30

Glu Gly Arg Gly Val Gly Asp Ile Asp Ala Ser Thr Asp Tyr Asn Asn
        35                  40                  45

Glu Asp Ala Leu Leu Asn Asp Glu Thr Arg Gln Pro Leu Ser Arg Lys
    50                  55                  60

Val Pro Leu Pro Ser Ser Arg Ile Asn Pro Tyr Arg Asn Val Ile Val
65                  70                  75                  80
```

-continued

```
Leu Arg Leu Val Val Leu Ser Ile Phe Leu His Tyr Arg Ile Thr Asn
                85                  90                  95

Pro Val Arg Asn Ala Tyr Pro Leu Trp Leu Leu Ser Val Ile Cys Glu
            100                 105                 110

Ile Trp Phe Ala Leu Ser Trp Leu Ile Asp Gln Phe Pro Lys Trp Phe
        115                 120                 125

Pro Ile Asn Arg Glu Thr Tyr Leu Asp Arg Leu Ala Leu Arg Tyr Asp
    130                 135                 140

Arg Glu Gly Glu Pro Ser Gln Leu Ala Ala Val Asp Ile Phe Val Ser
145                 150                 155                 160

Thr Val Asp Pro Met Lys Glu Pro Pro Leu Val Thr Ala Asn Thr Val
                165                 170                 175

Leu Ser Ile Leu Ala Val Asp Tyr Pro Val Asp Lys Val Ser Cys Tyr
            180                 185                 190

Val Ser Asp Asp Gly Ala Ala Met Leu Thr Phe Asp Ala Leu Ala Glu
        195                 200                 205

Thr Ser Glu Phe Ala Arg Lys Trp Val Pro Phe Val Lys Lys Tyr Asn
    210                 215                 220

Ile Glu Pro Arg Ala Pro Glu Trp Tyr Phe Ser Gln Lys Ile Asp Tyr
225                 230                 235                 240

Leu Lys Asp Lys Val His Pro Ser Phe Val Lys Asp Arg Arg Ala Met
                245                 250                 255

Lys Arg Glu Tyr Glu Glu Phe Lys Val Arg Ile Asn Gly Leu Val Ala
            260                 265                 270

Lys Ala Gln Lys Val Pro Glu Glu Gly Trp Ile Met Gln Asp Gly Thr
        275                 280                 285

Pro Trp Pro Gly Asn Asn Thr Arg Asp His Pro Gly Met Ile Gln Val
    290                 295                 300

Phe Leu Gly His Ser Gly Gly Leu Asp Thr Glu Gly Asn Glu Leu Pro
305                 310                 315                 320

Arg Leu Val Tyr Val Ser Arg Glu Lys Arg Pro Gly Phe Gln His His
                325                 330                 335

Lys Lys Ala Gly Ala Met Asn Ala Leu Val Arg Val Ser Ala Val Leu
            340                 345                 350

Thr Asn Gly Gln Tyr Met Leu Asn Leu Asp Cys Asp His Tyr Ile Asn
        355                 360                 365

Asn Ser Lys Ala Leu Arg Glu Ala Met Cys Phe Leu Met Asp Pro Asn
    370                 375                 380

Leu Gly Arg Ser Val Cys Tyr Val Gln Phe Pro Gln Arg Phe Asp Gly
385                 390                 395                 400

Ile Asp Arg Asn Asp Arg Tyr Ala Asn Arg Asn Thr Val Phe Phe Asp
                405                 410                 415

Ile Asn Leu Arg Gly Leu Asp Gly Ile Gln Gly Pro Val Tyr Val Gly
            420                 425                 430

Thr Gly Cys Val Phe Asn Arg Thr Ala Leu Tyr Gly Tyr Glu Pro Pro
        435                 440                 445

Ile Lys Gln Lys Lys Lys Gly Ser Phe Leu Ser Ser Leu Cys Gly Gly
    450                 455                 460

Arg Lys Lys Ala Ser Lys Ser Lys Lys Lys Ser Ser Asp Lys Lys Lys
465                 470                 475                 480

Ser Asn Lys His Val Asp Ser Ala Val Pro Val Phe Asn Leu Glu Asp
                485                 490                 495

Ile Glu Glu Gly Val Glu Gly Ala Gly Phe Asp Asp Glu Lys Ser Leu
```

-continued

```
            500                 505                 510

Leu Met Ser Gln Met Ser Leu Glu Lys Arg Phe Gly Gln Ser Ala Ala
        515                 520                 525

Phe Val Ala Ser Thr Leu Met Glu Tyr Gly Gly Val Pro Gln Ser Ala
    530                 535                 540

Thr Pro Glu Ser Leu Leu Lys Glu Ala Ile His Val Ile Ser Cys Gly
545                 550                 555                 560

Tyr Glu Asp Lys Thr Glu Trp Gly Thr Glu Ile Gly Trp Ile Tyr Gly
                565                 570                 575

Ser Val Thr Glu Asp Ile Leu Thr Gly Phe Lys Met His Ala Arg Gly
            580                 585                 590

Trp Arg Ser Ile Tyr Cys Met Pro Lys Arg Pro Ala Phe Lys Gly Ser
        595                 600                 605

Ala Pro Ile Asn Leu Ser Asp Arg Leu Asn Gln Val Leu Arg Trp Ala
    610                 615                 620

Leu Gly Ser Val Glu Ile Leu Phe Ser Arg His Cys Pro Ile Trp Tyr
625                 630                 635                 640

Gly Tyr Gly Gly Arg Leu Lys Phe Leu Glu Arg Phe Ala Tyr Ile Asn
                645                 650                 655

Thr Thr Ile Tyr Pro Leu Thr Ser Ile Pro Leu Leu Ile Tyr Cys Val
            660                 665                 670

Leu Pro Ala Ile Cys Leu Leu Thr Gly Lys Phe Ile Ile Pro Glu Ile
        675                 680                 685

Ser Asn Phe Ala Ser Ile Trp Phe Ile Ser Leu Phe Ile Ser Ile Phe
    690                 695                 700

Ala Thr Gly Ile Leu Glu Met Arg Trp Ser Gly Val Gly Ile Asp Glu
705                 710                 715                 720

Trp Trp Arg Asn Glu Gln Phe Trp Val Ile Gly Gly Ile Ser Ala His
                725                 730                 735

Leu Phe Ala Val Phe Gln Gly Leu Leu Lys Val Leu Ala Gly Ile Asp
            740                 745                 750

Thr Asn Phe Thr Val Thr Ser Lys Ala Ser Asp Glu Asp Gly Asp Phe
        755                 760                 765

Ala Glu Leu Tyr Met Phe Lys Trp Thr Thr Leu Leu Ile Pro Pro Thr
    770                 775                 780

Thr Ile Leu Ile Ile Asn Leu Val Gly Val Val Ala Gly Ile Ser Tyr
785                 790                 795                 800

Ala Ile Asn Ser Gly Tyr Gln Ser Trp Gly Pro Leu Phe Gly Lys Leu
                805                 810                 815

Phe Phe Ala Phe Trp Val Ile Val His Leu Tyr Pro Phe Leu Lys Gly
            820                 825                 830

Leu Met Gly Arg Gln Asn Arg Thr Pro Thr Ile Val Val Val Trp Ala
        835                 840                 845

Ile Leu Leu Ala Ser Ile Phe Ser Leu Leu Trp Val Arg Ile Asp Pro
    850                 855                 860

Phe Thr Thr Arg Val Thr Gly Pro Asp Thr Gln Thr Cys Gly Ile Asn
865                 870                 875                 880

Cys
```

```
<210> SEQ ID NO: 9
<211> LENGTH: 723
<212> TYPE: PRT
<213> ORGANISM: Acetobacter xylinum
```

-continued

```
<400> SEQUENCE: 9

Met Pro Glu Val Arg Ser Ser Thr Gln Ser Glu Ser Gly Met Ser Gln
 1               5                  10                  15

Trp Met Gly Lys Ile Leu Ser Ile Arg Gly Ala Gly Leu Thr Ile Gly
            20                  25                  30

Val Phe Gly Leu Cys Ala Leu Ile Ala Ala Thr Ser Val Thr Leu Pro
        35                  40                  45

Pro Glu Gln Gln Leu Ile Val Ala Phe Val Cys Val Val Ile Phe Phe
    50                  55                  60

Ile Val Gly His Lys Pro Ser Arg Arg Ser Gln Ile Phe Leu Glu Val
65                  70                  75                  80

Leu Ser Gly Leu Val Ser Leu Arg Tyr Leu Thr Trp Arg Leu Thr Glu
                85                  90                  95

Thr Leu Ser Phe Asp Thr Trp Leu Gln Gly Leu Leu Gly Thr Met Leu
            100                 105                 110

Leu Val Ala Glu Leu Tyr Ala Leu Met Met Leu Phe Leu Ser Tyr Phe
        115                 120                 125

Gln Thr Ile Ala Pro Leu His Arg Ala Pro Leu Pro Leu Pro Pro Asn
    130                 135                 140

Pro Asp Glu Trp Pro Thr Val Asp Ile Phe Val Pro Thr Tyr Asn Glu
145                 150                 155                 160

Glu Leu Ser Ile Val Arg Leu Thr Val Leu Gly Ser Leu Gly Ile Asp
                165                 170                 175

Trp Pro Pro Glu Lys Val Arg Val His Ile Leu Asp Asp Gly Arg Arg
            180                 185                 190

Pro Glu Phe Ala Ala Phe Ala Ala Glu Cys Gly Ala Asn Tyr Ile Ala
        195                 200                 205

Arg Pro Thr Asn Glu His Ala Lys Ala Gly Asn Leu Asn Tyr Ala Ile
    210                 215                 220

Gly His Thr Asp Gly Asp Tyr Ile Leu Ile Phe Asp Cys Asp His Val
225                 230                 235                 240

Pro Thr Arg Ala Phe Leu Gln Leu Thr Met Gly Trp Met Val Glu Asp
                245                 250                 255

Pro Lys Ile Ala Leu Met Gln Thr Pro His His Phe Tyr Ser Pro Asp
            260                 265                 270

Pro Phe Gln Arg Asn Leu Ser Ala Gly Tyr Arg Thr Pro Pro Glu Gly
        275                 280                 285

Asn Leu Phe Tyr Gly Val Val Gln Asp Gly Asn Asp Phe Trp Asp Ala
    290                 295                 300

Thr Phe Phe Cys Gly Ser Cys Ala Ile Leu Arg Arg Thr Ala Ile Glu
305                 310                 315                 320

Gln Ile Gly Gly Phe Ala Thr Gln Thr Val Thr Glu Asp Ala His Thr
                325                 330                 335

Ala Leu Lys Met Gln Arg Leu Gly Trp Ser Thr Ala Tyr Leu Arg Ile
            340                 345                 350

Pro Leu Ala Gly Gly Leu Ala Thr Glu Arg Leu Ile Leu His Ile Gly
        355                 360                 365

Gln Arg Val Arg Trp Ala Arg Gly Met Leu Gln Ile Phe Arg Ile Asp
    370                 375                 380

Asn Pro Leu Phe Gly Arg Gly Leu Ser Trp Gly Gln Arg Leu Cys Tyr
385                 390                 395                 400

Leu Ser Ala Met Thr Ser Phe Leu Phe Ala Val Pro Arg Val Ile Phe
                405                 410                 415
```

-continued

```
Leu Ser Ser Pro Leu Ala Phe Leu Phe Phe Gly Gln Asn Ile Ile Ala
            420                 425                 430

Ala Ser Pro Leu Ala Leu Leu Ala Tyr Ala Ile Pro His Met Phe His
        435                 440                 445

Ala Val Gly Thr Ala Ser Lys Ile Asn Lys Gly Trp Arg Tyr Ser Phe
    450                 455                 460

Trp Ser Glu Val Tyr Glu Thr Thr Met Ala Leu Phe Leu Val Arg Val
465                 470                 475                 480

Thr Ile Val Thr Leu Leu Ser Pro Ser Arg Gly Lys Phe Asn Val Thr
                485                 490                 495

Asp Lys Gly Gly Leu Leu Glu Lys Gly Tyr Phe Asp Leu Gly Ala Val
            500                 505                 510

Tyr Pro Asn Ile Ile Leu Gly Leu Ile Met Phe Gly Gly Leu Ala Arg
        515                 520                 525

Gly Val Tyr Glu Leu Ser Phe Gly His Leu Asp Gln Ile Ala Glu Arg
    530                 535                 540

Ala Tyr Leu Leu Asn Ser Ala Trp Ala Met Leu Ser Leu Ile Ile Ile
545                 550                 555                 560

Leu Ala Ala Ile Ala Val Gly Arg Glu Thr Gln Gln Lys Arg Asn Ser
                565                 570                 575

His Arg Ile Pro Ala Thr Ile Pro Val Glu Val Ala Asn Ala Asp Gly
            580                 585                 590

Ser Ile Ile Val Thr Gly Val Thr Glu Asp Leu Ser Met Gly Gly Ala
        595                 600                 605

Ala Val Lys Met Ser Trp Pro Ala Lys Leu Ser Gly Pro Thr Pro Val
    610                 615                 620

Tyr Ile Arg Thr Val Leu Asp Gly Glu Glu Leu Ile Leu Pro Ala Arg
625                 630                 635                 640

Ile Ile Arg Ala Gly Asn Gly Arg Gly Ile Phe Ile Trp Thr Ile Asp
                645                 650                 655

Asn Leu Gln Gln Glu Phe Ser Val Ile Arg Leu Val Phe Gly Arg Ala
            660                 665                 670

Asp Ala Trp Val Asp Leu Gly Gln Leu Gln Gly Arg Pro Pro Ala Ala
        675                 680                 685

Gln Pro His Gly His Gly Ser Gln Arg Gln Gly Pro Val Pro Phe Lys
    690                 695                 700

Trp Arg Tyr Arg Pro Ser Gln Phe Pro Asn Gln Ala Phe Gly Trp Gln
705                 710                 715                 720

Cys Pro Val


<210> SEQ ID NO: 10
<211> LENGTH: 756
<212> TYPE: PRT
<213> ORGANISM: acetobacter xylinum

<400> SEQUENCE: 10

Met Ser Glu Val Gln Ser Pro Val Pro Thr Glu Ser Arg Leu Gly Arg
 1               5                  10                  15

Ile Ser Asn Lys Ile Leu Ser Leu Arg Gly Ala Ser Tyr Ile Val Gly
            20                  25                  30

Ala Leu Gly Leu Cys Ala Leu Ile Ala Ala Thr Thr Val Thr Leu Asn
        35                  40                  45

Asn Asn Glu Gln Leu Ile Val Ala Ala Val Cys Val Val Ile Phe Phe
    50                  55                  60
```

-continued

```
Val Val Gly Arg Gly Lys Ser Arg Arg Thr Gln Ile Phe Leu Glu Val
65                  70                  75                  80

Leu Ser Ala Leu Val Ser Leu Arg Tyr Leu Thr Trp Arg Leu Thr Glu
                85                  90                  95

Thr Leu Asp Phe Asn Thr Trp Ile Gln Gly Ile Leu Gly Val Ile Leu
            100                 105                 110

Leu Met Ala Glu Leu Tyr Ala Leu Tyr Met Leu Phe Leu Ser Tyr Phe
        115                 120                 125

Gln Thr Ile Gln Pro Leu His Arg Ala Pro Leu Pro Leu Pro Asp Asn
    130                 135                 140

Val Asp Asp Trp Pro Thr Val Asp Ile Phe Ile Pro Thr Tyr Asp Glu
145                 150                 155                 160

Gln Leu Ser Ile Val Arg Leu Thr Val Leu Gly Ala Leu Gly Ile Asp
                165                 170                 175

Trp Pro Pro Asp Lys Val Asn Val Tyr Ile Leu Asp Asp Gly Val Arg
            180                 185                 190

Pro Glu Phe Glu Gln Phe Ala Lys Asp Cys Gly Ala Leu Tyr Ile Gly
        195                 200                 205

Arg Val Asp Val Asp Ser Ala His Ala Lys Ala Gly Asn Leu Asn His
    210                 215                 220

Ala Ile Lys Arg Thr Ser Gly Asp Tyr Ile Leu Ile Leu Asp Cys Asp
225                 230                 235                 240

His Ile Pro Thr Arg Ala Phe Leu Gln Ile Ala Met Gly Trp Met Val
                245                 250                 255

Ala Asp Arg Lys Ile Ala Leu Met Gln Thr Pro His His Phe Tyr Ser
            260                 265                 270

Pro Asp Pro Phe Gln Arg Asn Leu Ala Val Gly Tyr Arg Thr Pro Pro
        275                 280                 285

Glu Gly Asn Leu Phe Tyr Gly Val Ile Gln Asp Gly Asn Asp Phe Trp
    290                 295                 300

Asp Ala Thr Phe Phe Cys Gly Ser Cys Ala Ile Leu Arg Arg Glu Ala
305                 310                 315                 320

Ile Glu Ser Ile Gly Gly Phe Ala Val Glu Thr Val Thr Glu Asp Ala
                325                 330                 335

His Thr Ala Leu Arg Met Gln Arg Arg Gly Trp Ser Thr Ala Tyr Leu
            340                 345                 350

Arg Ile Pro Val Ala Ser Gly Leu Ala Thr Glu Arg Leu Thr Thr His
        355                 360                 365

Ile Gly Gln Arg Met Arg Trp Ala Arg Gly Met Ile Gln Ile Phe Arg
    370                 375                 380

Val Asp Asn Pro Met Leu Gly Arg Gly Leu Lys Leu Gly Gln Arg Leu
385                 390                 395                 400

Cys Tyr Leu Ser Ala Met Thr Ser Phe Phe Phe Ala Ile Pro Arg Val
                405                 410                 415

Ile Phe Leu Ala Ser Pro Leu Ala Phe Leu Phe Ala Gly Gln Asn Ile
            420                 425                 430

Ile Ala Ala Ala Pro Leu Ala Val Ala Ala Tyr Ala Leu Pro His Met
        435                 440                 445

Phe His Ser Ile Ala Thr Ala Ala Lys Val Asn Lys Gly Trp Arg Tyr
    450                 455                 460

Ser Phe Trp Ser Glu Val Tyr Glu Thr Thr Met Ala Leu Phe Leu Val
465                 470                 475                 480
```

-continued

```
Arg Val Thr Ile Val Thr Leu Leu Phe Pro Ser Lys Gly Lys Phe Asn
                485                 490                 495

Val Thr Glu Lys Gly Gly Val Leu Glu Glu Glu Glu Phe Asp Leu Gly
            500                 505                 510

Ala Thr Tyr Pro Asn Ile Ile Phe Ala Thr Ile Met Met Gly Gly Leu
        515                 520                 525

Leu Ile Gly Leu Phe Glu Leu Ile Val Arg Phe Asn Gln Leu Asp Val
    530                 535                 540

Ile Ala Arg Asn Ala Tyr Leu Leu Asn Cys Ala Trp Ala Leu Ile Ser
545                 550                 555                 560

Leu Ile Ile Leu Phe Ala Ala Ile Ala Val Gly Arg Glu Thr Lys Gln
                565                 570                 575

Val Arg Tyr Asn His Arg Val Glu Ala His Ile Pro Val Thr Val Tyr
            580                 585                 590

Asp Ala Pro Ala Glu Gly Gln Pro His Thr Tyr Tyr Asn Ala Thr His
        595                 600                 605

Gly Met Thr Gln Asp Val Ser Met Gly Gly Val Ala Val His Ile Pro
    610                 615                 620

Leu Pro Asp Val Thr Thr Gly Pro Val Lys Lys Arg Ile His Ala Val
625                 630                 635                 640

Leu Asp Gly Glu Glu Ile Asp Ile Pro Ala Thr Met Leu Arg Cys Thr
                645                 650                 655

Asn Gly Lys Ala Val Phe Thr Trp Asp Asn Asn Asp Leu Asp Thr Glu
            660                 665                 670

Arg Asp Ile Val Arg Phe Val Phe Gly Arg Ala Asp Ala Trp Leu Gln
        675                 680                 685

Trp Asn Asn Tyr Glu Asp Asp Arg Pro Leu Arg Ser Leu Trp Ser Leu
    690                 695                 700

Leu Leu Ser Ile Lys Ala Leu Phe Arg Lys Lys Gly Lys Ile Met Ala
705                 710                 715                 720

Asn Ser Arg Pro Lys Lys Lys Pro Leu Ala Leu Pro Val Glu Arg Arg
                725                 730                 735

Glu Pro Thr Thr Ile His Ser Gly Gln Thr Gln Glu Gly Lys Ile Ser
            740                 745                 750

Arg Ala Ala Ser
        755


<210> SEQ ID NO: 11
<211> LENGTH: 693
<212> TYPE: PRT
<213> ORGANISM: Escherichia coli

<400> SEQUENCE: 11

Met Leu Leu Trp Gly Val Ala Leu Ile Val Arg Arg Met Pro Gly Arg
 1               5                  10                  15

Phe Ser Ala Leu Met Leu Ile Val Leu Ser Leu Thr Val Ser Cys Arg
            20                  25                  30

Tyr Ile Trp Trp Arg Tyr Thr Ser Thr Leu Asn Trp Asp Asp Pro Val
        35                  40                  45

Ser Leu Val Cys Gly Leu Ile Leu Leu Phe Ala Ile Thr Tyr Ala Trp
    50                  55                  60

Ile Val Leu Val Leu Gly Tyr Phe Gln Val Val Trp Pro Leu Asn Arg
65                  70                  75                  80

Gln Pro Val Pro Leu Pro Lys Asp Met Ser Leu Trp Pro Ser Val Asp
                85                  90                  95
```

-continued

```
Ile Phe Val Pro Thr Tyr Asn Glu Asp Leu Asn Val Val Lys Asn Thr
            100                 105                 110

Ile Tyr Ala Ser Leu Gly Ile Asp Trp Pro Lys Asp Lys Leu Asn Ile
        115                 120                 125

Trp Ile Leu Asp Asp Gly Gly Arg Glu Glu Phe Arg Gln Phe Ala Gln
    130                 135                 140

Asn Val Gly Val Lys Tyr Ile Ala Arg Thr Thr His Glu His Ala Lys
145                 150                 155                 160

Ala Gly Asn Ile Asn Asn Ala Leu Lys Tyr Ala Lys Gly Glu Phe Val
                165                 170                 175

Ser Ile Phe Asp Cys Asp His Val Pro Thr Arg Ser Phe Leu Gln Met
            180                 185                 190

Thr Met Gly Trp Phe Leu Lys Glu Lys Gln Leu Ala Met Met Gln Thr
        195                 200                 205

Pro His His Phe Phe Ser Pro Asp Pro Phe Glu Arg Asn Leu Gly Arg
    210                 215                 220

Phe Arg Lys Thr Pro Asn Glu Gly Thr Leu Phe Tyr Gly Leu Val Gln
225                 230                 235                 240

Asp Gly Asn Asp Met Trp Asp Ala Thr Phe Phe Cys Gly Ser Cys Ala
                245                 250                 255

Val Ile Arg Arg Lys Pro Leu Asp Glu Ile Gly Gly Ile Ala Val Glu
            260                 265                 270

Thr Val Thr Glu Asp Ala His Thr Ser Leu Arg Leu His Arg Arg Gly
        275                 280                 285

Tyr Thr Ser Ala Tyr Met Arg Ile Pro Gln Ala Ala Gly Leu Ala Thr
    290                 295                 300

Glu Ser Leu Ser Ala His Ile Gly Gln Arg Ile Arg Trp Ala Arg Gly
305                 310                 315                 320

Met Val Gln Ile Phe Arg Leu Asp Asn Pro Leu Thr Gly Lys Gly Leu
                325                 330                 335

Lys Phe Ala Gln Arg Leu Cys Tyr Val Asn Ala Met Phe His Phe Leu
            340                 345                 350

Ser Gly Ile Pro Arg Leu Ile Phe Leu Thr Ala Pro Leu Ala Phe Leu
        355                 360                 365

Leu Leu His Ala Tyr Ile Ile Tyr Ala Pro Ala Leu Met Ile Ala Leu
    370                 375                 380

Phe Val Leu Pro His Met Ile His Ala Ser Leu Thr Asn Ser Lys Ile
385                 390                 395                 400

Gln Gly Lys Tyr Arg His Ser Phe Trp Ser Glu Ile Tyr Glu Thr Val
                405                 410                 415

Leu Ala Trp Tyr Ile Ala Pro Pro Thr Leu Val Ala Leu Ile Asn Pro
            420                 425                 430

His Lys Gly Lys Phe Asn Val Thr Ala Lys Gly Gly Gly Leu Val Glu
        435                 440                 445

Glu Glu Tyr Val Asp Trp Val Ile Ser Arg Pro Tyr Ile Phe Leu Val
    450                 455                 460

Leu Leu Asn Leu Val Gly Val Ala Val Gly Ile Trp Arg Tyr Phe Tyr
465                 470                 475                 480

Gly Pro Pro Thr Glu Met Leu Thr Val Val Val Ser Met Val Trp Val
                485                 490                 495

Phe Tyr Asn Leu Ile Val Leu Gly Gly Ala Val Ala Val Ser Val Glu
            500                 505                 510
```

-continued

```
Ser Lys Gln Val Arg Arg Ser His Arg Val Glu Met Thr Met Pro Ala
        515                 520                 525

Ala Ile Ala Arg Glu Asp Gly His Leu Phe Ser Cys Thr Val Gln Asp
    530                 535                 540

Phe Ser Asp Gly Gly Leu Gly Ile Lys Ile Asn Gly Gln Ala Gln Ile
545                 550                 555                 560

Leu Glu Gly Gln Lys Val Asn Leu Leu Leu Lys Arg Gly Gln Gln Glu
                565                 570                 575

Tyr Val Phe Pro Thr Gln Val Ala Arg Val Met Gly Asn Glu Val Gly
            580                 585                 590

Leu Lys Leu Met Pro Leu Thr Thr Gln Gln His Ile Asp Phe Val Gln
        595                 600                 605

Cys Thr Phe Ala Arg Ala Asp Thr Trp Ala Leu Trp Gln Asp Ser Tyr
    610                 615                 620

Pro Glu Asp Lys Pro Leu Glu Ser Leu Leu Asp Ile Leu Lys Leu Gly
625                 630                 635                 640

Phe Arg Gly Tyr Arg His Leu Ala Glu Phe Ala Pro Ser Ser Val Lys
                645                 650                 655

Gly Ile Phe Arg Val Leu Thr Ser Leu Val Ser Trp Val Val Ser Phe
            660                 665                 670

Ile Pro Pro Arg Pro Glu Arg Ser Glu Thr Ala Gln Pro Ser Asp Gln
        675                 680                 685

Ala Leu Ala Gln Gln
    690


<210> SEQ ID NO: 12
<211> LENGTH: 861
<212> TYPE: PRT
<213> ORGANISM: Agrobacterium tumefaciens

<400> SEQUENCE: 12

Met Cys Arg Cys Gly Arg Ala Val Arg Ser Arg Pro Val Cys Arg Pro
 1               5                  10                  15

Gly Gln Leu Val Val Arg Arg Ser Pro Arg Pro Arg Ser Arg Asn His
            20                  25                  30

Ser Arg Cys Arg Pro Leu Arg Leu Ser Val Phe Pro Arg Pro His Arg
        35                  40                  45

Arg Val Arg His His Cys Gln Arg Asp Leu Arg Trp Glu Pro Gly Arg
    50                  55                  60

Trp Ile Ala Val Arg Trp Lys Ala Ala Arg Ser His Arg Arg Phe Arg
65                  70                  75                  80

Arg Cys Pro Phe Pro Arg Gln Leu Val Trp Pro Val Arg Glu Arg His
                85                  90                  95

Arg Asp Ala Gly Asp Arg Arg Asn Gln Arg Glu Arg Arg Arg Arg Asp
            100                 105                 110

Ala Tyr His Glu Ile Ser Glu Pro Lys Phe Arg Thr Arg Lys Arg Thr
        115                 120                 125

Glu Ser Phe Trp Met Asn Lys Ala Ile Thr Val Ile Val Trp Leu Leu
    130                 135                 140

Val Ser Leu Cys Val Leu Ala Ile Ile Thr Met Pro Val Ser Leu Gln
145                 150                 155                 160

Thr His Leu Val Ala Thr Ala Ile Ser Leu Ile Leu Leu Ala Thr Ile
                165                 170                 175

Lys Ser Phe Asn Gly Gln Gly Ala Trp Arg Leu Val Ala Leu Gly Phe
            180                 185                 190
```

```
Gly Thr Ala Ile Val Leu Arg Tyr Val Tyr Trp Arg Thr Thr Ser Thr
        195                 200                 205

Leu Pro Pro Val Asn Gln Leu Glu Asn Phe Ile Pro Gly Phe Leu Leu
    210                 215                 220

Tyr Leu Ala Glu Met Tyr Ser Val Val Met Leu Gly Leu Ser Leu Val
225                 230                 235                 240

Ile Val Ser Met Pro Leu Pro Ser Arg Lys Thr Arg Pro Gly Ser Pro
                245                 250                 255

Asp Tyr Arg Pro Thr Val Asp Val Phe Val Pro Ser Tyr Asn Glu Asp
            260                 265                 270

Ala Glu Leu Leu Ala Asn Thr Leu Ala Ala Ala Lys Asn Met Asp Tyr
        275                 280                 285

Pro Ala Asp Arg Phe Thr Val Trp Leu Leu Asp Asp Gly Gly Ser Val
    290                 295                 300

Gln Lys Arg Asn Ala Ala Asn Ile Val Glu Ala Gln Ala Ala Gln Arg
305                 310                 315                 320

Arg His Glu Glu Leu Lys Lys Leu Cys Glu Asp Leu Asp Val Arg Tyr
                325                 330                 335

Leu Thr Arg Glu Arg Asn Val His Ala Lys Ala Gly Asn Leu Asn Asn
            340                 345                 350

Gly Leu Ala His Ser Thr Gly Glu Leu Val Thr Val Phe Asp Ala Asp
        355                 360                 365

His Ala Pro Ala Arg Asp Phe Leu Leu Glu Thr Val Gly Tyr Phe Asp
    370                 375                 380

Glu Asp Pro Arg Leu Phe Leu Val Gln Thr Pro His Phe Phe Val Asn
385                 390                 395                 400

Pro Asp Pro Ile Glu Arg Asn Leu Arg Thr Phe Glu Thr Met Pro Ser
                405                 410                 415

Glu Asn Glu Met Phe Tyr Gly Ile Ile Gln Arg Gly Leu Asp Lys Trp
            420                 425                 430

Asn Gly Ala Phe Phe Cys Gly Ser Ala Ala Val Leu Arg Arg Glu Ala
        435                 440                 445

Leu Gln Asp Ser Asp Gly Phe Ser Gly Val Ser Ile Thr Glu Asp Cys
    450                 455                 460

Glu Thr Ala Leu Ala Leu His Ser Arg Gly Trp Asn Ser Val Tyr Val
465                 470                 475                 480

Asp Lys Pro Leu Ile Ala Gly Leu Gln Pro Ala Thr Phe Ala Ser Phe
                485                 490                 495

Ile Gly Gln Arg Ser Arg Trp Ala Gln Gly Met Met Gln Ile Leu Ile
            500                 505                 510

Phe Arg Gln Pro Leu Phe Lys Arg Gly Leu Ser Phe Thr Gln Arg Leu
        515                 520                 525

Cys Tyr Met Ser Ser Thr Leu Phe Trp Leu Phe Pro Phe Pro Arg Thr
    530                 535                 540

Ile Phe Leu Phe Ala Pro Leu Phe Tyr Leu Phe Phe Asp Leu Gln Ile
545                 550                 555                 560

Phe Val Ala Ser Gly Gly Glu Phe Leu Ala Tyr Thr Ala Ala Tyr Met
                565                 570                 575

Leu Val Asn Leu Met Met Gln Asn Tyr Leu Tyr Gly Ser Phe Arg Trp
            580                 585                 590

Pro Trp Ile Ser Glu Leu Tyr Glu Tyr Val Gln Thr Val His Leu Leu
        595                 600                 605
```

-continued

```
Pro Ala Val Val Ser Val Ile Phe Asn Pro Gly Lys Pro Thr Phe Lys
    610                 615                 620

Val Thr Ala Lys Asp Glu Ser Ile Ala Glu Ala Arg Leu Ser Glu Ile
625                 630                 635                 640

Ser Arg Pro Phe Phe Val Ile Phe Ala Leu Leu Leu Val Ala Met Ala
                645                 650                 655

Phe Ala Val Trp Arg Ile Tyr Ser Glu Pro Tyr Lys Ala Asp Val Thr
            660                 665                 670

Leu Val Val Gly Gly Trp Asn Leu Leu Asn Leu Ile Phe Ala Gly Cys
        675                 680                 685

Ala Leu Gly Val Val Ser Glu Arg Gly Asp Lys Ser Ala Ser Arg Arg
    690                 695                 700

Ile Thr Val Lys Arg Arg Cys Glu Val Gln Leu Gly Gly Ser Asp Thr
705                 710                 715                 720

Trp Val Pro Ala Ser Ile Asp Asn Val Ser Val His Gly Leu Leu Ile
                725                 730                 735

Asn Ile Phe Asp Ser Ala Thr Asn Ile Glu Lys Gly Ala Thr Ala Ile
            740                 745                 750

Val Lys Val Lys Pro His Ser Glu Gly Val Pro Glu Thr Met Pro Leu
        755                 760                 765

Asn Val Val Arg Thr Val Arg Gly Glu Gly Phe Val Ser Ile Gly Cys
    770                 775                 780

Thr Phe Ser Pro Gln Arg Ala Val Asp His Arg Leu Ile Ala Asp Leu
785                 790                 795                 800

Ile Phe Ala Asn Ser Glu Gln Trp Ser Glu Phe Gln Arg Val Arg Arg
                805                 810                 815

Lys Lys Pro Gly Leu Ile Arg Gly Thr Ala Ile Phe Leu Ala Ile Ala
            820                 825                 830

Leu Phe Gln Thr Gln Arg Gly Leu Tyr Tyr Leu Val Arg Ala Arg Arg
        835                 840                 845

Pro Ala Pro Lys Ser Ala Lys Pro Val Gly Ala Val Lys
    850                 855                 860
```

COTTON AND RICE CELLULOSE SYNTHASE DNA SEQUENCES

RELATED APPLICATIONS

This application claims priority to U.S. Provisional Application Ser. No. 60/029,987 filed Oct. 29, 1996.

INTRODUCTION

1. Technical Field

This invention relates to plant cellulose synthase cDNA encoding sequences, and their use in modifying plant phenotypes. Methods are provided whereby the sequences can be used to control or limit the expression of endogenous cellulose synthase.

This invention also relates to methods of using in vitro constructed DNA transcription or expression cassettes capable of directing fiber-tissue transcription of a DNA sequence of interest in plants to produce fiber cells having an altered phenotype, and to methods of providing for or modifying various characteristics of cotton fiber. The invention is exemplified by methods of using cotton fiber promoters for altering the phenotype of cotton fiber, and cotton fibers produced by the method.

2. Background

In spite of much effort, no one has succeeded in isolating and characterizing the enzyme(s) responsible for synthesis of the major cell wall polymer of plants, cellulose.

Numerous efforts have been directed toward the study of synthesis of cellulose (1,4-β-D-glucan) in higher plants. However, hampered by low rates of activity in vitro, the cellulose synthase of plants has resisted purification and detailed characterization (for reviews, see 1,2). Aided by the discovery of cyclic-di-GMP as a specific activator, the cellulose synthase of the bacterium *Acetobacter xylinum* can be easily assayed in vitro, has been purified to homogeneity, and a catalytic subunit identified (for reviews, see 2,3). Furthermore, an operon of four genes involved in cellulose synthesis in *A. xylinum* has been cloned (4–7).

Characterization of these genes indicates that the first gene, termed either BcsA (7) or AcsAB (6) codes for the 83 kD subunit of the cellulose synthase that binds the substrate UDP-glc and presumably catalyzes the polymerization of glucose residues to 1,4-β-D-glucan (8). The second gene (B) of the operon is believed to function as a regulatory subunit binding cyclic-di-GMP (9) while recent evidence suggests that the C and D genes may code for proteins that form a pore allowing secretion of the polymer and control the pattern of crystallization of the resulting microfibrils (6).

Recent studies with another gram-negative bacterium, *Agrobacterium tumefaciens*, have also led to cloning of genes involved in cellulose synthesis (10,11), although the proposed pathway of synthesis differs in some respects from that of *A. xylinum*. In *A. tumefaciens*, a CelA gene showing significant homology to the BcsA/AcsAB gene of *A. xylinum*, is proposed to transfer glc from UDP-glc to a lipid acceptor; other gene products may then build up a lipid oligosaccharide that is finally polymerized to cellulose by the action of an endo-glucanase functioning in a synthetic mode. In addition, homologs of the CelA, B, and C genes have been identified in *E. coli*, but, as this organism is not known to synthesize cellulose in vivo, the function of these genes is not clear (2).

These successes in bacterial systems opened the possibility that homologs of the bacterial genes might be identified in higher plants. However, experments in a number of laboratories utilizing the *A. xylinum* genes as probes for screening plant cDNA libraries have failed to identify similar plant genes. Such lack of success suggests that, if plants do contain homologs of the bacterial genes, their overall sequence homology is not very high. Recent studies analyzing the conserved motifs common to glycosyltransferases using either UDP-glc or UDP-GlcNAc as substrate suggest that there are specific conserved regions that might be expected to be found in any plant homolog of the catalytic subunit (referred to hereafter as CelA). In one of these studies, Delmer and Amor (2) identifed a motif common to many such glycosyltransferases including the bacterial CelA proteins. An independent analysis (6) also concluded that this motif was highly conserved in a group of similar glycosyltransferases.

Extending these studies further, Saxena et al. (12) presented an elegant model for the mechanism of catalysis for enzymes such as cellulose synthase that have the unique problem of synthesizing consecutive residues that are rotated approximately 180° with respect to each other. The model invokes independent UDP-glc binding sites and, based upon hydrophobic cluster analysis of these enzymes, the authors concluded that 3 critical regions in all such processive glycosyltransferases each contain a conserved aspartate (D) residue, while a fourth region contained a conserved QXXRW motif. The first D residue resides in the motif as previously analyzed (2,6).

In general, genetic engineering techniques have been directed to modifying the phenotype of individual prokaryotic and eukaryotic cells, especially in culture. Plant cells have proven more intransigent than other eukaryotic cells, due not only to a lack of suitable vector systems but also as a result of the different goals involved. For many applications, it is desirable to be able to control gene expression at a particular stage in the growth of a plant or in a particular plant part. For this purpose, regulatory sequences are required which afford the desired initiation of transcription in the appropriate cell types and/or at the appropriate time in the plant's development without having serious detrimental effects on plant development and productivity. It is therefore of interest to be able to isolate sequences which can be used to provide the desired regulation of transcription in a plant cell during the growing cycle of the host plant.

One aspect of this interest is the ability to change the phenotype of particular cell types, such as differentiated epidermal cells that originate in fiber tissue, i.e. cotton fiber cells, so as to provide for altered or improved aspects of the mature cell type. Cotton is a plant of great commercial significance. In addition to the use of cotton fiber in the production of textiles, other uses of cotton include food preparation with cotton seed oil and animal feed derived from cotton seed husks.

A related goal involving the control of cell wall and characteristics would be to affect valuable secondary tree characteristics of wood for paper forestry products. For instance, by altering the balance of cellulose and lignin, the quality of wood for paper production may be improved.

Finally, despite the importance of cotton as a crop, the breeding and genetic engineering of cotton fiber phenotypes has taken place at a relatively slow rate because of the absence of reliable promoters for use in selectively effecting changes in the phenotype of the fiber. In order to effect the desired phenotypic changes, transcription initiation regions capable of initiating transcription in fiber cells during development are desired. Thus, an important goal of cotton bioengineering research is the acquisition of a reliable promoter which would permit expression of a protein selectively in cotton fiber to affect such qualities as fiber strength, length, color and dyability.

Relevant Literature

Cotton fiber-specific promoters are discussed in PCT publications WO 94/12014 and WO 95/08914, and John and Crow, Proc. Natl. Acad. Sci. USA, 89:5769–5773, 1992. cDNA clones that are preferentially expressed in cotton fiber have been isolated. One of the clones isolated corresponds to mRNA and protein that are highest during the late primary cell wall and early secondary cell wall synthesis stages. John and Crow, supra.

In plants, control of cytoskeletal organization is poorly understood in spite of its importance for the regulation of patterns of cell division, expansion, and subsequent deposition of secondary cell wall polymers. The cotton fiber represents an excellent system for studying cytoskeletal organization. Cotton fibers are single cells in which cell elongation and secondary wall deposition can be studied as distinct events. These fibers develop synchronously within the boll following anthesis, and each fiber cell elongates for about 3 weeks, depositing a thin primary wall (Meinert and Delmer, (1984) Plant Physiol. 59: 1088–1097; Basra and Malik, (1984) Int Rev of Cytol 89: 65–113). At the time of transition to secondary wall cellulose synthesis, the fiber cells undergo a synchronous shift in the pattern of cortical microtubule and cell wall microfibril alignments, events which may be regulated upstream by the organization of actin (Seagull, (1990) Protoplasma 159: 44–59; and (1992) In: Proceedings of the Cotton Fiber Cellulose Conference, National Cotton Council of America, Memphis RN, pp 171–192.

Agrobacterium-mediated cotton transformation is described in Umbeck, U.S. Pat. Nos. 5,004,863 and 5,159, 135 and cotton transformation by particle bombardment is reported in WO 92/15675, published Sep. 17, 1992. Transformation of Brassica has been described by Radke et al. (Theor. Appl. Genet. (1988) 75;685–694; Plant Cell Reports (1992) 11:499–505.

Genes involved in lignin biosynthesis are described by Dwivedi, U. N., Campbell, W. H., Yu, J., Datla, R. S. S., Chiang, V. L., and Podila, G. K. (1994) "Modification of lignin biosynthesis in transgenic Nicotiana through expression of an antisense O-methyltransferase gene from Populus" Pl. Mol. Biol. 26: 61–71; and Tsai, C. J., Podila, G. K. and Chaing, V. L. (1995) "Nucleotide sequence of Populus tremuloides gene for caffeic acid/5 hydroxyferulic acid O-methyltransferase" Pl. Physiol. 107: 1459; and also U.S. Pat. No. 5,451,514 (claiming the use of cinnamyl alcohol dehydrogenase gene in an antisense orientation such that the endogenous plant cinnamyl alcohol dehydrogenase gene is inhibited).

OTHER REFERENCES CITED THROUGHOUT THE SPECIFICATION

1. Gibeaut, D. M., & Carpita, N. C. (1994) FASEB J. 8, 904–915.
2. Delmer, D. P., & Amor, Y. (1995) Plant Cell 7, 987–1000.
3. Ross, P., Mayer, R., & Benziman, M. (1991) Microbiol. Rev. 55, 35–58.
4. Saxena, I. M., Lin, F. C., & Brown, R. M., Jr. (1990) Plant Mol. Biol. 15, 673–683.
5. Saxena, I. M., Lin, F. C., & Brown, R. M., Jr. (1992) Plant Mol. Biol. 16, 947–954.
6. Saxena, I. M., Kudlicka, K., Okuda, K., & Brown, R. M., Jr. (1994) J. Bacteriol. 176, 5735–5752.
7. Wong, H. C., Fear, A. L., Calhoon,, R. D., Eidhinger, G. H., Mayer, R., Amikam, D., Benziman, M., Gelfand, D. H., Meade, J. H., Emerick, A. W., Bruner, R., Ben-Basat, B. A., & Tal, R. (1990) Proc. Natl. Acad. Sci. USA 87, 8130–8134.
8. Lin, F.-C., Brown, R. M. Jr., Drake, R. R. Jr., & Haley, B. E. (1990) J. Biol. Chem. 265, 4782–4784.
9. Mayer, R., Ross, P., Winhouse, H., Amikam, D., Volman, G., Ohana, P., Calhoon, R. D., Wong, H. C., Emerick, A. W., & Benziman, M. (1991) Proc. Natl. Acad. Sci. USA 88, 5472–5476.
10. Matthysse, A. G., White, S., & Lightfoot, R. (1995a) J. Bacteriol. 177, 1069–1075.
11. Matthysse, A. G., Thomas, D. O. L. , & White, S. (1995b) J. Bacteriol. 177, 1076–1081.
12. Saxena, I. M., Brown, R. M., Jr., Fevre, M., Geremia, R. A., & Henrissat, B. (1995) J. Bacteriol. 177, 1419–1424.
13. Meinert, M., & Delmer, D. P. (1977) Plant Physiol. 59, 1088–1097.
14. Delmer, D. P., Pear, J. R., Andrawis, A., & Stalker, D. M. (1995) Mol. Gen. Genet. 248, 43–51.
15. Delmer, D. P., Solomon, M., & Read, S. M. (1991) Plant Physiol. 95, 556–563.
16. Nagai, K., & Thogersen, H. C. (1987) Methods in Enzymol. 153, 461–481.
17. Laemmli, U. K. (1970) Nature 227, 680–685.
18. Kyte, J., & Doolittle, R. F. (1982) J. Mol. Biol. 157, 105–132. 19. Oikonomakos, N. G., Acharya, K. R., Stuart, D. I., Melpidou, A. E., McLaughlin, P. J., & Johnson, L. N. (1988) Eur. J. Biochem. 173, 569–578.
20. Maltby, D., Carpita, N. C., Montezinos, D., Kulow, C., & Delmer, D. P. (1979) Plant Physiol. 63, 1158–1164.
21. Inoue, S. B., Takewaki, N., Takasuka, T., Mio, T., Adachi, M., Fujii, Y., Miyamoto, C., Arisawa, M., Furuichi, Y., & Watanabe, T. (1995) Eur. J. Biochem. 231, 845–854.
22. Jacob, S. R., & Northcote, D. H. (1985) J. Cell Sci. 2 (suppl.), 1–11.
23. Delmer, D. P. (1987) Annu. Rev. Plant Physiol. 38, 259–290.
24. Altschul, S. F., Gish, W., Miller, W., Myers, E. W., & Lipman, D. J. (1990) J. Mol. Biol. 215, 403–410
25. Milligan, G., Parenti, M., & Magee, A. I. (1995) TIBS 20, 183–186.
26. Amor, Y., Haigler, C. H., Johnson, S., Wainscott, M., & Delmer, D. P. (1995) Proc. Natl. Acad. Sci. USA 92, 9353–9357.
27. Amor, Y., Mayer, R., Benziman, M., & Delmer, D. P. (1991) Plant Cell 3, 989–995.

SUMMARY OF THE INVENTION

Two cotton genes, CelA1 and CelA2, have been shown to be highly expressed in developing fibers at the onset of secondary wall cellulose synthesis. Comparisons indicate that these genes and the rice CelA gene encode polypeptides that have three regions of reasonably high homology, both in terms of primary amino acid sequence and hydropathy, with bacterial CelA proteins. The fact that these homologous stretches are in the same sequential order as in the bacterial CelA proteins and also contain four sub-regions previously predicted to be critical for substrate binding and catalysis (12) argues that the plant genes encode true homologs of bacterial CelA proteins. Furthermore, the pattern of expression in fiber as well as our demonstration that at least one of these highly-conserved regions is critical for UDP-glc binding also supports this conclusion.

Novel DNA promoter sequences are also supplied, and methods for their use are described for directing transcription of a gene of interest in cotton fiber.

The developing cotton fiber is an excellent system for studies on cellulose synthesis as these single cells develop synchronously in the boll and, at the end of elongation, initiate the synthesis of a nearly pure cellulosic cell wall. During this transition period, synthesis of other cell wall polymers ceases and the rate of cellulose synthesis is estimated to rise nearly 100-fold in vivo (13). In our continuing efforts to identify genes critical to this phase of fiber development, we have initiated a program sequencing randomly selected cDNA clones derived from a library prepared from mRNA harvested from fibers at the stage in which secondary wall synthesis approaches its maximum rate (approximately 21 dpa).

We have characterized two cotton (*Gossypium hirsutum*) cDNA clones and identified one rice (*Oryza sativa*) cDNA that are homologs of the bacterial CelA genes that encode the catalytic subunit of cellulose synthase. Three regions in the deduced amino acid sequences of the plant CelA gene products are conserved with respect to the proteins encoded by bacterial CelA genes. Within these conserved regions are four highly conserved subdomains previously suggested to be critical for catalysis and/or binding of the substrate UDP-glc. An overexpressed DNA segment of the cotton CelA1 gene encodes a polypeptide fragment that spans these domains and effectively binds UDP-glc, while a similar fragment having one of these domains deleted does not. The plant CelA genes show little homology at the amino and carboxy terminal regions and also contain two internal insertions of sequence, one conserved and one hypervariable, that are not found in the bacterial gene sequences. Cotton CelA1 and CelA2 genes are expressed at high levels during active secondary wall cellulose synthesis in the developing fiber. Genomic Southern analyses in cotton demonstrate that CelA comprises a family of approximately four distinct genes.

We report here the discovery of two cotton genes that show highly-enhanced expression at the time of onset of secondary wall synthesis in the fiber. The sequences of these two cDNA clones, termed CelA1 and CelA2, while not identical, are highly homologous to each other and to a sequenced rice EST clone discovered in the dBEST databank. The deduced proteins also share signifigant regions of homology with the bacterial CelA proteins. Coupled with their high level and specificity of expression in fiber at the time of active cellulose synthesis, as well as the ability of an *E. coli* expressed fragment of the CelA1 gene product to bind UDP-glc, these findings support the conclusion that these plant genes are true homologs of the bacterial CelA genes.

The methods of the present invention include transfecting a host plant cell of interest with a transcription or expression cassette comprising a cotton fiber promoter and generating a plant which is grown to produce fiber having the desired phenotype. Constructs and methods of the subject invention thus find use in modulation of endogenous fiber products, as well as production of exogenous products and in modifying the phenotype of fiber and fiber products. The constructs also find use as molecular probes. In particular, constructs and methods for use in gene expression in cotton embryo tissues are considered herein. By these methods, novel cotton plants and cotton plant parts, such as modified cotton fibers, may be obtained.

The sequences and constructs of this invention may also be used to isolate related cellulose synthase genes from forest tree species, for use in transforming and modifying wood quality. As and example, lignin, an undesirable by-product of the pulping process, by be reduced by overexpressing the cellulose synthase product and diverting production into cellulose.

Thus, the application provides constructs and methods of use relating to modification of cell and cell wall phenotype in cotton fiber and wood products.

BRIEF DESCRIPTION OF THE DRAWINGS

FIG. 3. Multiple alignment of deduced amino acid sequences of plant and bacterial CelA proteins (*G. Hirsutum* CelA-1 (SEQ ID NO:6); *G. Hirsutum* CelA-2 (SEQ ID NO:7); *O. Sativa* CelA (SEQ ID NO:8); *A. Xylinum* AcsAB (SEQ ID NO:9); *A. Xylinum* Bcsa (SEQ ID NO:10); *E. coli* ORF f692 (SEQ ID NO:11); and *A. tumefaciens* CelA (SEQ ID NO: 12)). Analyses were performed by Clustal Analysis using the Lasergene Multalign program (DNAStar, Madison, Wis.) with gap and gap-length penalties of 10 and a PAM250 weight table. Residues are boxed and shaded when they show chemical group similarity in 4 out of 7 proteins compared. H-1, H-2, H-3 regions are indicated where homology between plant and bacterial proteins is highest. The plant proteins show two insertions that are not present in the bacterial protein—one, P-CR, is conserved among the plant CelA genes, while a second insertion is hypervariable (HVR) between plant genes. The presence of the P-CR and HVR regions led to inaccurate alignments when the entire proteins were compared; the optimal alignments shown here were thus performed in five seperate blocks. Regions U-1 through U-4 are predicted to be critical for UDP-glc binding and catalysis in bacterial CelA proteins; the predicted critical D residues and QXXRW motif are boxed and starred respectively. Potential sites of N-glycosylation are indicate by -G-.

FIGS. 6A–6E. Nucleic acid sequences (SEQ ID NO:1) to cDNA of CelA1 protein of cotton (*Gossypium hirsutum*).

FIGS. 7A–7D. Nucleic acid sequences (SEQ ID NO:2) to cDNA of CelA2 protein of cotton (*Gossypium hirsutum*), including approximately the last 3' two-thirds of the encoding region.

FIGS. 8A–8B. Genomic nucleic acid sequences (SEQ ID NO:3) of CelA1 protein of cotton (*Gossypium hirsutum*), including approximately 900 bases of the promoter region 5' to the encoding sequences.

DETAILED DESCRIPTION OF THE INVENTION

Figure 1:
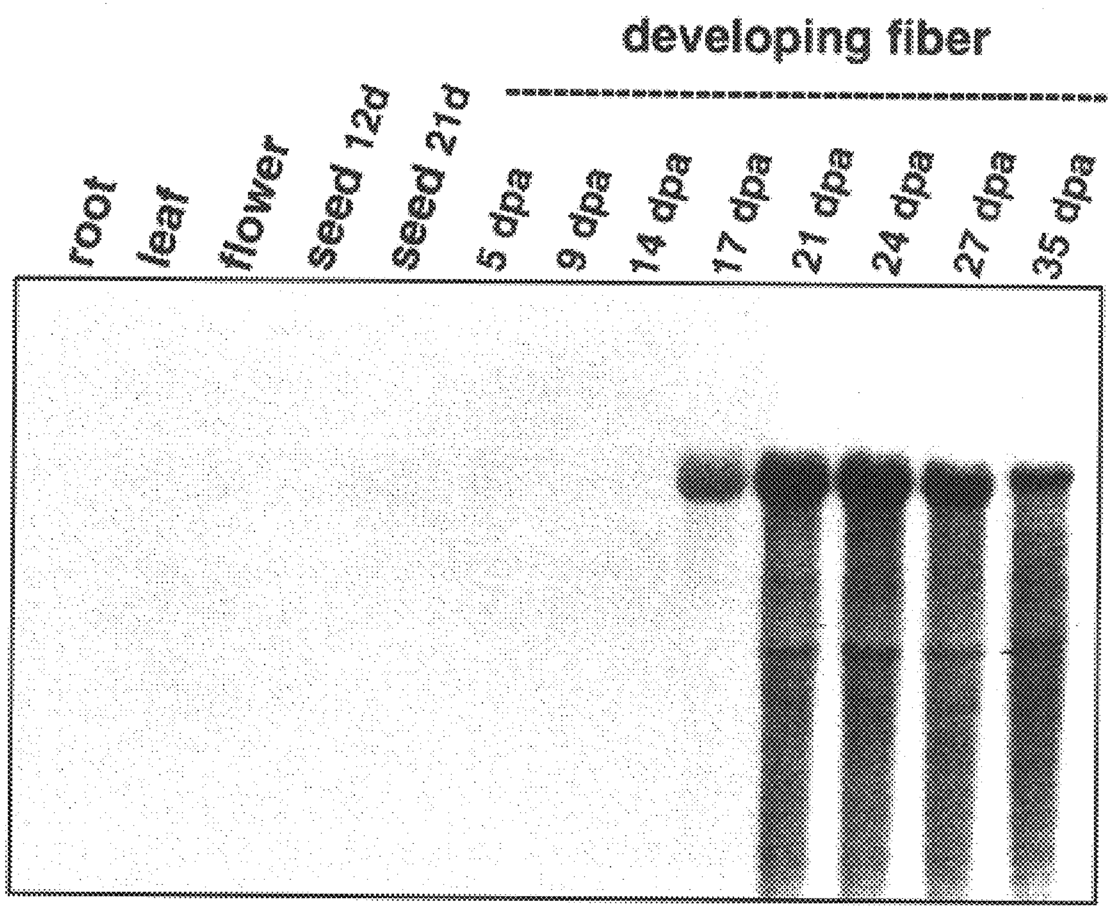
FIG. 1. Northern analysis of CelA1 gene in cotton tissues and developing fiber. Approximately 10 μg total RNA from each tissue was loaded per lane. Blots were prepared and probe preparation and hybridization conditions were performed as described previously (14). The entire CelA1 cDNA insert was used as a probe in this experiment. Exposure time for the audoradiogram was seven hours at −70°.

In accordance with the subject invention, novel constructs and methods are described, which may be used provide for transcription of a nucleotide sequence of interest in cells of a plant host, preferentially in cotton fiber cells to produce cotton fiber having an altered color phenotype.

Cotton fiber is a differentiated single epidermal cell of the outer integument of the ovule. It has four distinct growth phases; initiation, elongation (primary cell wall synthesis), secondary cell wall synthesis, and maturation. Initiation of fiber development appears to be triggered by hormones. The primary cell wall is laid down during the elongation phase, lasting up to 25 days postanthesis (DPA). Synthesis of the secondary wall commences prior to the cessation of the elongation phase and continues to approximately 40 DPA, forming a wall of almost pure cellulose.

The constructs for use in such cells may include several forms, depending upon the intended use of the construct. Thus, the constructs include vectors, transcriptional cassettes, expression cassettes and plasmids. The transcriptional and translational initiation region (also sometimes referred to as a "promoter"), preferably comprises a transcriptional initiation regulatory region and a translational initiation regulatory region of untranslated 5' sequences, "ribosome binding sites," responsible for binding mRNA to ribosomes and translational initiation. It is preferred that all of the transcriptional and translational functional elements of the initiation control region are derived from or obtainable from the same gene. In some embodiments, the promoter will be modified by the addition of sequences, such as enhancers, or deletions of nonessential and/or undesired sequences. By "obtainable" is intended a promoter having a DNA sequence sufficiently similar to that of a native promoter to provide for the desired specificity of transcription of a DNA sequence of interest. It includes natural and synthetic sequences as well as sequences which may be a combination of synthetic and natural sequences.

Cotton fiber transcriptional initiation regions of cellulose synthase are used in cotton fiber modification.

A transcriptional cassette for transcription of a nucleotide sequence of interest in cotton fiber will include in the direction of transcription, the cotton fiber transcriptional initiation region, a DNA sequence of interest, and a transcriptional termination region functional in the plant cell. When the cassette provides for the transcription and translation of a DNA sequence of interest it is considered an expression cassette. One or more introns may be also be present.

Other sequences may also be present, including those encoding transit peptides and secretory leader sequences as desired.

Downstream from, and under the regulatory control of, the cellulose synthase transcriptional/translational initiation control region is a nucleotide sequence of interest which provides for modification of the phenotype of fiber. The nucleotide sequence may be any open reading frame encoding a polypeptide of interest, for example, an enzyme, or a sequence complementary to a genomic sequence, where the genomic sequence may be an open reading frame, an intron, a noncoding leader sequence, or any other sequence where the complementary sequence inhibits transcription, messenger RNA processing, for example, splicing, or translation. The nucleotide sequences of this invention may be synthetic, naturally derived, or combinations thereof. Depending upon the nature of the DNA sequence of interest, it may be desirable to synthesize the sequence with plant preferred codons. The plant preferred codons may be determined from the codons of highest frequency in the proteins expressed in the largest amount in the particular plant species of interest. Phenotypic modification can be achieved by modulating production either of an endogenous transcription or translation product, for example as to the amount, relative distribution, or the like, or an exogenous transcription or translation product, for example to provide for a novel function or products in a transgenic host cell or tissue. Of particular interest are DNA sequences encoding expression products associated with the development of plant fiber, including genes involved in metabolism of cytokinins, auxins, ethylene, abscissic acid, and the like. Methods and compositions for modulating cytokinin expression are described in U.S. Pat. No. 5,177,307, which disclosure is hereby incorporated by reference. Alternatively, various genes, from sources including other eukaryotic or prokaryotic cells, including bacteria, such as those from *Agrobacterium tumefaciens* T-DNA auxin and cytokinin biosynthetic gene products, for example, and mammals, for example interferons, may be used.

Alternatively, the present invention provides the sequences to cotton cellulose synthase, which can be expressed, or down regulated by antisense or co-suppression with its own, or other cotton or other fiber promoters to modify fiber phenotyp.

In cotton, primary wall hemicellulose synthesis ceases as secondary wall synthesis initiates in the fiber, and there are only two possible β-glucans synthesized in fibers at the time these genes are highly-expressed; callose and cellulose (20). The following data strongly argue against the plant CelA genes coding for callose synthase: 1) callose synthase binds UDP-glc and is activated in a $Ca^{2+}$-dependent manner (2), while the CelA1 polypeptide fragment containing the UDP-glc binding site preferentially binds UDP-glc in a $Mg^2$+-dependent manner, similar to bacterial cellulose synthase (9); 2) the timing of synthesis of callose in vivo in developing cotton fiber (20) does not match the expression of the cotton CelA genes (FIG. 1); 3) comparison of the CelA gene sequences with those of suspected 1,3-β-glucan synthase genes from yeast (21) indicated no significant homology.

It is still possibille that the CelA protein might encode both activities, as hypothesized some years ago (22–23), and the plant CelAs might be responsible for direct polymerization of glucan from UDP-glc as proposed for *A. xylinum*, although they may catalyze synthesis of a lipid-glc precursor as proposed for the CelA protein of *A. tumefaciens.*

In addition to their similarities, the plant CelA genes show several very interesting divergences from their bacterial ancestors, and these may account for the previous lack of success in using bacterial probes to detect these cDNA clones. However, a BLAST search of protein data banks (24) using the entire protein sequence of cotton CelA1 always shows highest homology with the bacterial cellulose synthases. Of particular interest is the insertion of two unique, plant-specific regions designated P-CR and HVR. These regions are clearly not artifacts of cloning as they are observed in both cotton genes as well as the rice CelA gene. The three plant proteins show a high degree of amino acid homology to each other throughout most of their length, diverging only at the N- and C-terminal ends and the very interesting HVR region. It is tempting to speculate that the HVR region may confer some specificity of function; the highly-charged and cysteine rich nature of the first portion of HVR could make this region a potential candidate for interaction with specific regulatory proteins, for cytoskeletal elements, or for redox regulation. In addition, we note the presence of several cysteine residues near the N- and C-terminal regions of the protein that might serve as substrates for palmytolylation and also serve to help anchor the protein in the membrane (25).

In summary, the finding of these plant CelA homologs potentially opens up an exciting chapter in research on cellulose synthesis in higher plants. Their finding is of particular significance since biochemical approaches to identification of plant cellulose synthase have proven exceedingly difficult. One obvious challenge will be to gain definitive proof that these genes are truely functional in cellulose synthesisin vivo. Other promising goals will be to identify other components of a complex that might interact with CelA, such as that proposed for sucrose synthase (26), and/or a regulatory subunit that binds cyclic-di-GMP (9,27) or other glycosyltransferases (10,11).

Transcriptional cassettes may be used when the transcription of an anti-sense sequence is desired. When the expression of a polypeptide is desired, expression cassettes providing for transcription and translation of the DNA sequence of interest will be used. Various changes are of interest; these changes may include modulation (increase or decrease) of formation of particular saccharides, hormones, enzymes, or other biological parameters. These also include modifying the composition of the final fiber that is changing the ratio and/or amounts of water, solids, fiber or sugars. Other phenotypic properties of interest for modification include response to stress, organisms, herbicides, brushing, growth regulators, and the like. These results can be achieved by providing for reduction of expression of one or more endogenous products, particularly an enzyme or cofactor, either by producing a transcription product which is complementary (anti-sense) to the transcription product of a native gene, so as to inhibit the maturation and/or expression of the transcription product, or by providing for expression of a gene, either endogenous or exogenous, to be associated with the development of a plant fiber.

The termination region which is employed in the expression cassette will be primarily one of convenience, since the termination regions appear to be relatively interchangeable. The termination region may be native with the transcriptional initiation region, may be native with the DNA sequence of interest, may be derived from another source. The termination region may be naturally occurring, or wholly or partially synthetic. Convenient termination regions are available from the Ti-plasmid of *A. tumefaciens*, such as the octopine synthase and nopaline synthase termination regions. In some embodiments, it may be desired to use the 3' termination region native to the cotton fiber transcription initiation region used in a particular construct.

As described herein, in some instances additional nucleotide sequences will be present in the constructs to provide for targeting of a particular gene product to specific cellular locations.

Similarly, other constitutive promoters may also be useful in certain applications, for example the mas, Mac or DoubleMac, promoters described in U.S. Pat. No. 5,106,739 and by Comai et al., *Plant Mol. Biol.* (1990) 15:373–381). When plants comprising multiple gene constructs are desired, the plants may be obtained by co-transformation with both constructs, or by transformation with individual constructs followed by plant breeding methods to obtain plants expressing both of the desired genes.

A variety of techniques are available and known to those skilled in the art for introduction of constructs into a plant cell host. These techniques include transfection with DNA employing *A. tumefaciens* or *A. rhizogenes* as the transfecting agent, protoplast fusion, injection, electroporation, particle acceleration, etc. For transformation with Agrobacterium, plasmids can be prepared in *E. coli* which contain DNA homologous with the Ti-plasmid, particularly T-DNA. The plasmid may or may not be capable of replication in Agrobacterium, that is, it may or may not have a broad spectrum prokaryotic replication system such as does, for example, pRK290, depending in part upon whether the transcription cassette is to be integrated into the Ti-plasmid or to be retained on an independent plasmid. The Agrobacterium host will contain a plasmid having the vir genes necessary for transfer of the T-DNA to the plant cell and may or may not have the complete T-DNA. At least the right border and frequently both the right and left borders of the T-DNA of the Ti- or Ri-plasmids will be joined as flanking regions to the transcription construct. The use of T-DNA for transformation of plant cells has received extensive study and is amply described in EPA Serial. No. 120,516, Hoekema, In: The Binary Plant Vector System Offset-drukkerij Kanters B. V., Alblasserdam, 1985, Chapter V, Knauf, et al., Genetic Analysis of Host Range Expression by Agrobacterium, In: Molecular Genetics of the Bacteria-Plant Interaction, Puhler, A. ed., Springer-Verlag, New York, 1983, p. 245, and An, et al., *EMBO J.* (1985) 4:277–284.

For infection, particle acceleration and electroporation, a disarmed Ti-plasmid lacking particularly the tumor genes found in the T-DNA region) may be introduced into the plant cell. By means of a helper plasmid, the construct may be transferred to the *A. tumefaciens* and the resulting transfected organism used for transfecting a plant cell; explants may be cultivated with transformed *A. tumefaciens* or *A. rhizogenes* to allow for transfer of the transcription cassette to the plant cells. Alternatively, to enhance integration into the plant genome, terminal repeats of transposons may be used as borders in conjunction with a transposase. In this situation, expression of the transposase should be inducible, so that once the transcription construct is integrated into the genome, it should be relatively stably integrated. Transgenic plant cells are then placed in an appropriate selective medium for selection of transgenic cells which are then grown to callus, shoots grown and plantlets generated from the shoot by growing in rooting medium.

To confirm the presence of the transgenes in transgenic cells and plants, a Southern blot analysis can be performed using methods known to those skilled in the art. Expression products of the transgenes can be detected in any of a variety of ways, depending upon the nature of the product, and include immune assay, enzyme assay or visual inspection, for example to detect pigment formation in the appropriate plant part or cells. Once transgenic plants have been obtained, they may be grown to produce fiber having the desired phenotype. The fibers may be harvested, and/or the seed collected. The seed may serve as a source for growing additional plants having the desired characteristics. The terms transgenic plants and transgenic cells include plants and cells derived from either transgenic plants or transgenic cells.

The various sequences provided herein may be used as molecular probes for the isolation of other sequences which may be useful in the present invention, for example, to obtain related transcriptional initiation regions from the same or different plant sources. Related transcriptional initiation regions obtainable from the sequences provided in this invention will show at least about 60% homology, and more preferred regions will demonstrate an even greater percentage of homology with the probes.

Of particular importance is the ability to obtain related transcription initiation control regions having the timing and tissue parameters described herein. Thus, by employing the techniques described in this application, and other techniques known in the art (such as Maniatis, et al., *Molecular Cloning,—A Laboratory Manual* (Cold Spring Harbor, N.Y.) 1982), other encoding regions or transcription initiation regions of cellulose synthase as described in this invention may be determined. The constructs can also be used in conjunction with plant regeneration systems to obtain plant cells and plants; thus, the constructs may be used to modify the phenotype of fiber cells, to provide cotton fibers which are colored as the result of genetic engineering to heretofor unavailable hues and/or intensities.

Various varieties and lines of cotton may find use in the described methods. Cultivated cotton species include *Gossypium hirsutum* and *G. babadense* (extra-long stable, or Pima cotton), which evolved in the New World, and the Old World crops *G. herbaceum* and *G. arboreum.*

By using encoding sequences to enzymes which control wood quality and wood product characteristics, i.e., cellulose synthase and O-methyltransferase (a key enzyme in lignin biosynthesis) the relative synthesis of cellulose and lignin by plants may be controlled. Transformation of the plant genome with a recombinant gene construct which contains the gene specifying an enzyme critical to the synthesis of cellulose or lignin or a lignin precursor, in either a sense or in an antisense orientation. If an antisense orientation, the gene will transcribed so mRNA having a sequence complementary to the equivalent mRNA transcribed from the endogenous gene is expressed, leading to suppression of the synthesis of lignin or cellulose.

If the recombinant gene has the lignin enzyme gene in normal, or "sense" orientation, increased production of the enzyme may occur when the insert is the full length DNA but suppression may occur if only a partial sequence is employed.

Furthermore, the expression of one may be increased in this manner while the other is reduced. For instance, the production of cellulose may by increased through the over-expression of cellulose synthase, while lignin production is reduced. By thus reducing the relative lignin content, the quality of wood for paper production would be improved.

EXAMPLES

The following examples are offered by way of illustration and not by limitation.

Example 1 cDNA Libraries

An unamplified cDNA library was used to prepare the Lambda Uni-Zap vector (Stratagene, LaJolla, Calif.) using cDNA derived from polyA+mRNA prepared from fibers of *Gossypium hirsutum* Acala SJ-2 harvested at 21 DPA, the time at which secondary wall cellulose synthesis is approaching a maximal rate (13). Approximately 250 plaques were randomly selected from the cDNA library, phages purified and plasmids excised from the phage vector and transformed.

The resulting clones/inserts were size screened on 0.8% agarose gels (DNA inserts below 600bp were excluded).

Example 2

Isolation and Secuencing of cDNA Clones

Plasmid DNA inserts were randomly sequenced using an Applied Biosystems (Foster City, Calif.) Model 373A DNA sequencer. A search of the GenBank EST databank revealed that there were at least 23 rice and 8 Arabidopsis EST clones that contain sequences similar to the cotton CelA1 DNA sequence. EST clone S14965 was obtained from Y. Nagamura (Rice Genome Research Program, Tsukuba). A series of deletion mutants were generated and used for DNA sequencing analysis at the Weizmann Institute of Science (Rehovot).

Example 3

Northern and Southern Analyses

Cotton plants (*G. hirsutum* cv. Coker 130) were grown in the greenhouse and tissues harvested at the appropriate times indicated and frozen in liquid $N_2$. Total cotton RNA and cotton genomic DNA was prepared and subjected to Northern and Southern analyses as described previously (14).

Example 4

UDP-Glc Binding Studies

To construct a GST-CelA1 protein fusion, a 1.6 kb DNA CelA1 DNA fragment containing a putative cytoplasmic domain between the second and third transmembrane helices was PCR amplified with the primers ATTGAATTC-CTGGGTGTTGGATCAGTT (SEQ ID NO:4) and ATTCTCGAGTGGAAGGGATTGAAA (SEQ ID NO: 5) in a reaction containing 1 ng plasmid DNA (clone 213) as template. The amplified fragment was unidirectionally cloned into the EcoRI and XboI sites of the GST expression vector pGEX4T-3 (Pharmacia), generating a fusion protein GST-CS containing the amino acids Ser215 to Leu759 of the cotton CelA1 protein. Two CelA1 gene internal PstI sites within the plasmid pGST-CS were used to generate the deletion mutant pGST-CSAU1, which lacks 196 amino acids (and the U1 binding region) from Val252 to Ala447.

For the UDGP binding assays, $\alpha$-$^{32}$P-labeled UDP-glc was prepared as described (15). The two fusion proteins GST-CS and GST-CSAEU1 were expressed in *E. coli* and purified from inclusion bodies (16). Proteins were suspended in sample buffer, heated to 100-C. for 5 min and approximately 50 ng of the two fusion protein products and molecular weight standards (Bio-Rad) subjected to SDS-PAGE using 4.5% and 7.5% acrylamide in the stacking and separating gels, respectively (17). After electrophoresis, protein transfer to nitrocellulose filters was carried out in transfer buffer (25 mM Tris, 192 mM glycine and 20% (v/v) methanol). The filter was briefly rinsed in deionized $H_2O$ and incubated in PBS buffer for 15 min, then stained with Ponceau-S in PBS buffer. After washing in deionized $H_2O$, protein was further renatured on the filter by incubation in PBS buffer for 30 min and used directly for binding assays. All binding buffers contained 50 mM HEPES/KOH (pH 7.3), 50 mM NaCl and 1 mMDTT. In addition, binding buffers contained either 5 mM $MgCl_2$ and 5 mM EGTA (Buffer Mg/EGTA), 5 mM EDTA (Buffer EDTA) or 1 mM $CaCl_2$ and 20 mM cellobiose (Buffer Ca/CB). Binding reaction was carried out in 7 ml containing $^{32}$P-labeled UDP-glc ($1\times10^7$ cpm) at room temperature for 3 hours with constant shaking. Filters were washed separately three times in 20ml washing buffer consisting of 50 mM HEPES/KOH (pH 7.3) and 50 mM NaCl for 5 min each, briefly dried and analyzed on a Bio-imaging analyzer BAS1000 (Fugi).

Example 5

Identification, Differential Expression and Genomic Analysis of Cotton CelA Genes During the course of screening and sequencing random cDNA clones from a cotton fiber specific cDNA library prepared from RNA collected approximately 21 dpa, it was discovered that two cDNA clones that initially exhibited small blocks of amino acid homology to the proteins encoded by the bacterial CelA genes. Clone 213 appeared to be full-length cDNA while another distinct clone, 207, appeared to be a partial clone relative to the length of 213. These two clones were partially homologous at the nucleotide and amino acid levels and designated CelA1 and CelA2 respectively.

These clones were then utilized as probes for Northern blot analysis to determine their differential expression in cotton tissues and developing cotton fiber. FIG. 1 indicates the expression pattern for the CelA1 gene. The CelA1 gene encodes a mRNA of approximately 3.2 kb in length and is expressed at extremely high levels in developing fiber, beginning at approximately 17 dpa, the time at which secondary wall cellulose synthesis is initiated(13). The gene is also expressed at low levels in all other cotton tissues, most notably in root, flower and developing seeds. Since regions of these genes are somewhat homologous at the nucleotide level, gene specific probes were designed (using the hypervariable regions described in FIG. 3) to distinguish the specific expression patterns of CelA1 and CelA2. These gene specific probes generated expression patterns (data not shown) for the two genes identical to that shown in FIG. 1, except that a very low mRNA level was also detected in the primary wall phase of fiber development (5–14 dpa) for the CelA2 gene when the blots were overexposed. The CelA2 gene specific probe also encoded a 3.2 kb mRNA, analogous in size to the mRNA specified by the gene for CelA1. Messenger RNAs for both genes exhibit a characteristic degradation pattern similar to other mRNAs specifically expressed late in fiber development (J. Pear, unpublished observations) and this degradation is not a result of the integrity of the mRNA preparations (14). We estimate that both cotton CelA genes are expressed in developing fiber approximately 500 times their level of expression in other cotton tissues and that they constitute approximately 1–2% of the 24 dpa fiber mRNA.

Figure 2:
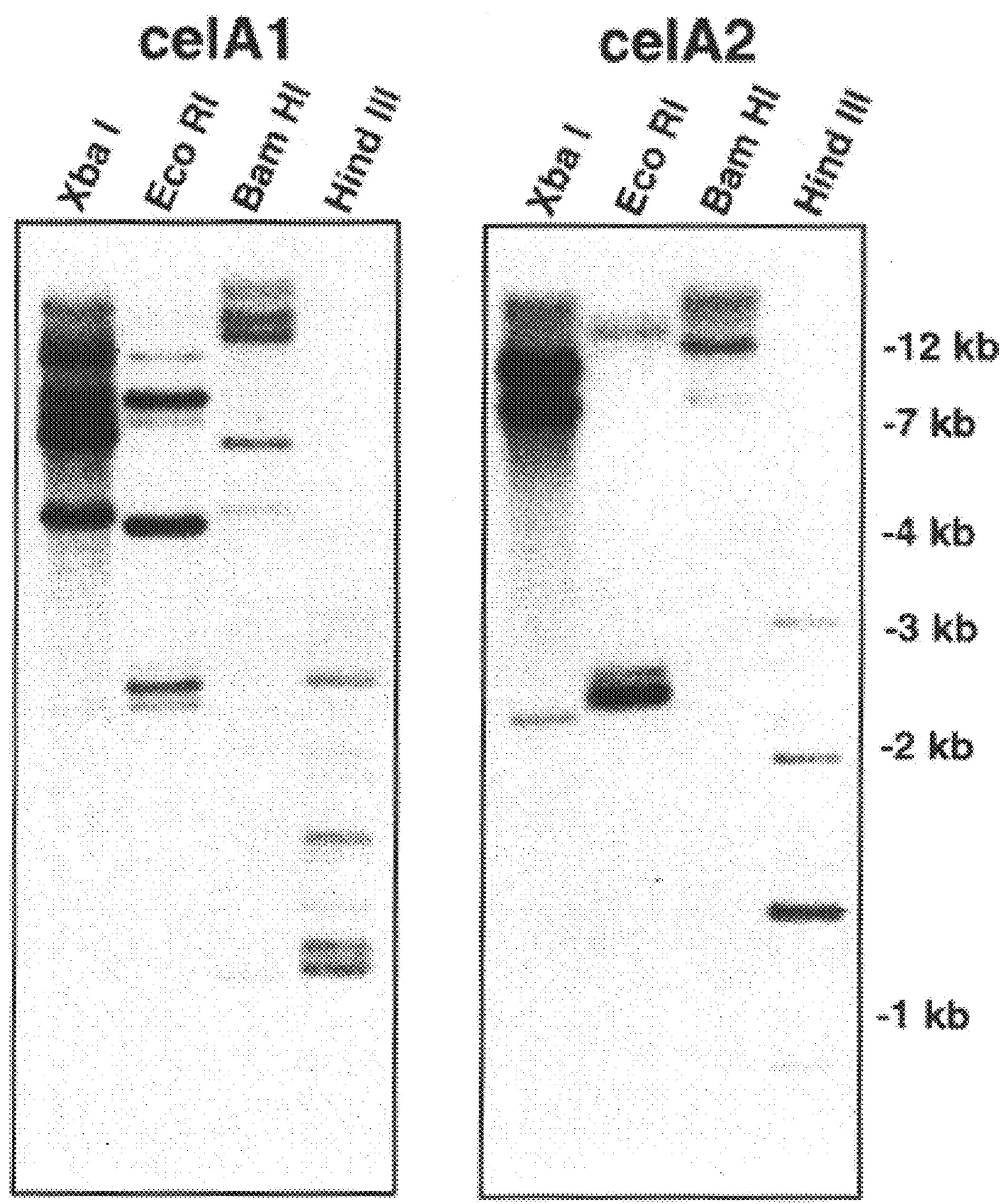
FIG. 2. Cotton genomic DNA analysis for both the CelA1 and CelA2 cDNAs. Approximately 10–12 μg of DNA was digested with the designated restriction enzymes and electrophoresed 0.9% agarose gels. Probe preparation and hybridization conditions were as described previously (14). The entire CelA1 and CelA2 cDNAs were utlized as probes. Exposure time for the audoradiograms was three days at −70°.

In order to estimate the number of CelA genes in the cotton genome, Southern analysis was performed utilizing both CelA cDNAS independently as probes (FIG. 2). Although the two cotton genes are fairly non-homologous at the nucleotide level over their entire length, there are regions of homology (the H1, H2 and H3 regions described below) and it was thought these regions could be useful in identifying other cotton CelA genes. FIG. 2 indicates that the CelA1 cDNA probe will hybridize, albeit weakly, to the CelA2 genomic equivalent and vise versa. The HindIII pattern for both genes and cDNA probes is particularly discriminating. There are also a number of other weakly hybridzing bands in these digests and from these data we estimate that the cotton CelA genes constitute a small family of approximately four genes. Homology of Plant and Bacterial CelA Gene Products.

Figure 3B:
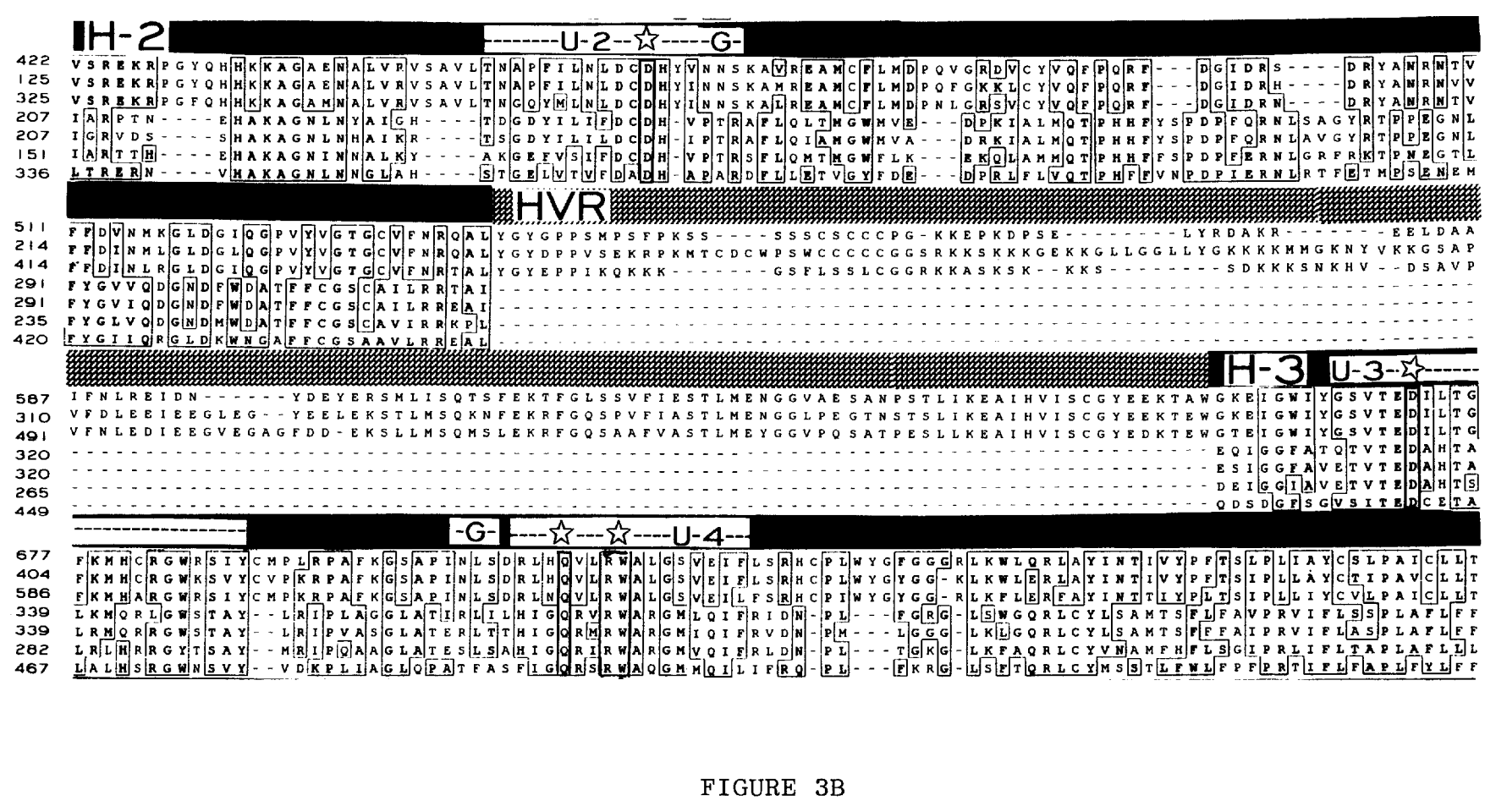
Figure 4:
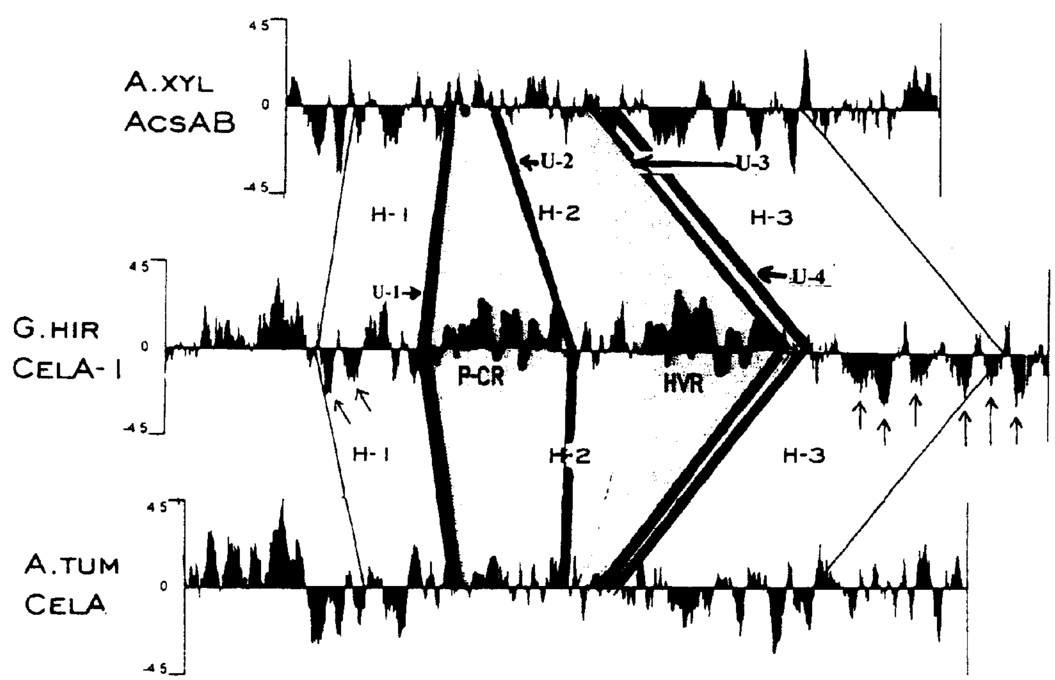
FIG. 4. Kyte-Doolittle hydropathy plots of cotton CelA1 aligned with those of two bacterial CelA proteins. Alignments and designations are based upon those noted in FIG. 2. The hydropathy profiles shown were calculated using a window of 7, although a window of 19 was used for predictions of transmembrane helices that are indicated by the arrows.

In addition to the two similar cotton CelA genes, a homologous cDNA clone was discovered in the dBest databank* of rice and Arabidopsis ESTs. Accession No. D48636, the rice clone having the longest insert was obtained and sequenced, and the homology comparisons with bacterial proteins reported here also include results with the rice CelA. FIG. 3 shows the results of a multiple alignment of the deduced amino acid sequences from the three plant CelA genes and four bacterial CelA genes from *A. xylinum* (AcsAB and BcsA), *E. coli*, and *A. tumefaciens*. FIG. 4 shows hydropathy plots (18) of cotton CelA1 similarly aligned with two bacterial CelA proteins and serves as a more general summary of the overall homologies.

*The following accession numbers were identified as showing homology with cotton CelA-1. For rice: D48636, D41261, D40691, D46824, D47622, D47175, D41766, D41986, D24655, D23732, D24375, D47732, D47821, D47850, D47494, D24964, D24862, D24860, D24711, D23841, D48053, D48612, D40673; for Arabidopsis: T45303, T45414, H6149, H36985, Z30729, H36425, T45311, A35212.

Of the plant genes, only the cotton CelA1 appears to be a full-length clone of 3.2 kb exhibiting an open reading frame that could potentially code for a polypeptide of 109,586 kD, a pI of 6.4, and four potential sites of N-glycosylation. Comparison of the N-terminal region of cotton CelA1 with bacterial genes indicates that the plant protein has an extended N-terminal similar in length and hydropathy profile, but with only poor amino acid sequence homology to the *A. tumefaciens* CelA protein. In general, sequence homology of plant and bacterial genes in both the N-terminal and C-terminal regions is poor. However, although overall similarity comparing plant to bacterial proteins is less than 25%, three homologous regions were identified, called H-1, H-2, and H-3, where the sequence similarity rises to 50–60% at the amino acid level. Interspersed between these regions of homology are two plant-specific regions not found at all in the bacterial proteins. Sequences in the first of these insertions are highly conserved in the plant genes (P-CR), while the second interspersed region seems to be a hypervariable regions (HVR) for there is considerable sequence divergence among the plant proteins analyzed.

Figure 5A:
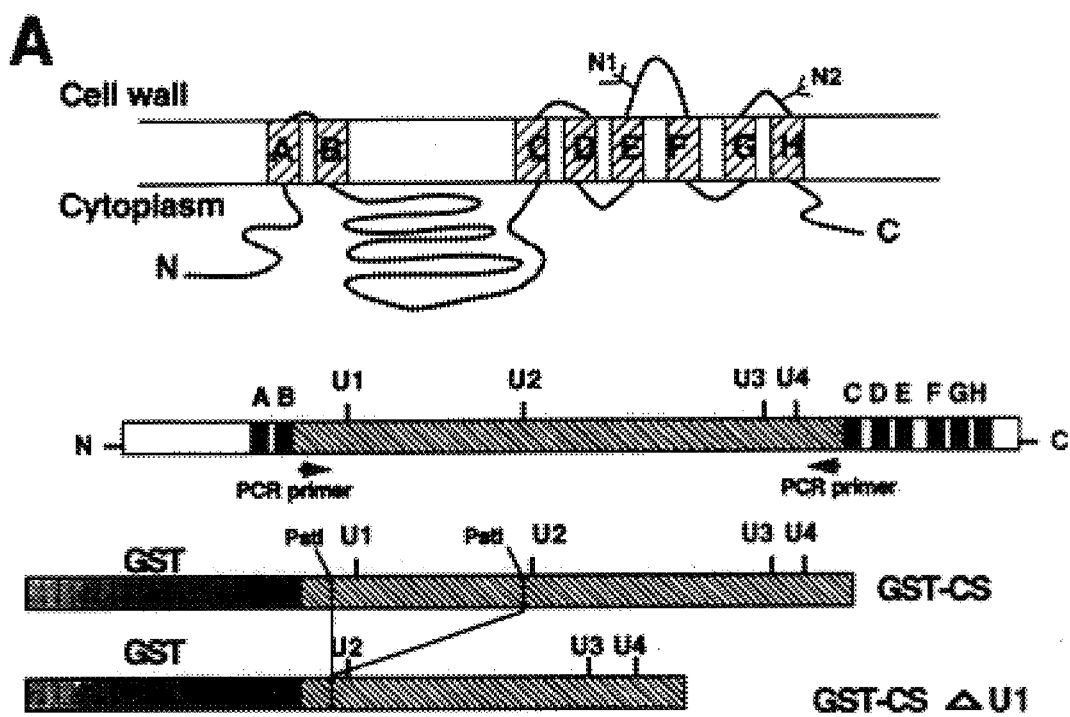
FIGS. 5A–5B. An *E. coli* expressed GST cotton CelA-1 fusion protein binds the containing U1 through U4 binds UDP-glc in vitro. Panel A shows a hypothetical orientation of the cotton CelA1 protein in the plasma membrane and indicates the cytoplasmic region containing the sub-domains U-1 to U-4. GST-fusion constructs for CelA1 fragments spanning the region between the potential transmembrane helices (A through H) were prepared as described in Materials and Methods. The purified and blotted CelA1 fusion protein fragments were tested as described in Materials and Methods for their ability to bind $^{32}$P-UDP-glc (panel B). M refers to the molecular weight markers while CS and AEU1 to the full-length and deleted GST-CelA1 fusion polypeptides. The left panel shows proteins stained with Coomassie blue while the other three panels show representative autoradiograms under different binding conditions as described in Materials and Methods. Ph, BSA and Ova refer to the molecular weight standards phosphorylase b, bovine serum albumin and ovalbumin respectively.
Figure 5B:
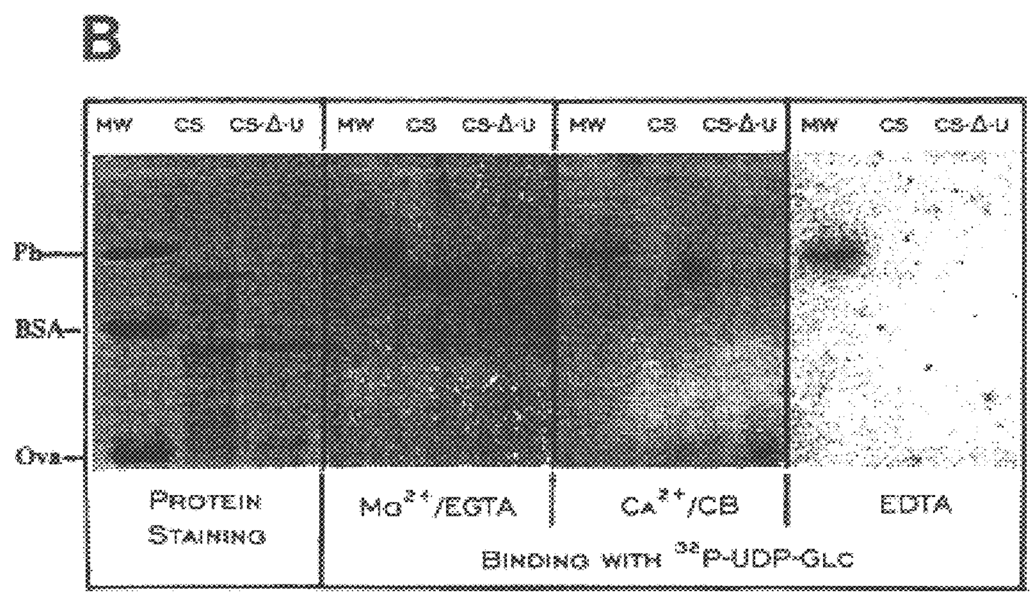

None of the plant or bacterial CelA proteins contains obvious signal sequences even though they are presumably transmembrane proteins (4). However, the overall profiles suggest two potential transmembrane helices in the N-terminal and six in the C-terminal region of the cotton CelA1 that could anchor the protein in the membrane (see arrows FIG. 3 and also panel A of FIG. 5). The amino acid sequence positions for these predicted transmembrane helices are: A (169–187), B (200–218), C (759–777), D (783–801), E (819–837), F (870–888), G (903–921), H (933–951). The central portions of the proteins are more hydrophilic and are predicted to reside in the cytoplasm and contain the site(s) of catalysis. More detailed inspection of these hydrophilic stretches reveals four particularly conserved sub-regions (marked U-1 through U-4 on FIGS. 3–4) that contain the conserved asp (D) residues (in U-1–3) and the motif QXXRW (in U-4) that have been proposed (12) to be involved in substrate binding and/or catalysis. Binding of UDP-glucose. Further evidence that the proteins encoded by these plant genes are CelA homologs comes from our demonstration that a DNA segment encoding the central region of the cotton CelA1 protein, over-expressed in *E. coli*, binds UDP-glc. We subcloned a 1.6 kb fragment of the cotton CelA1 clone to create a hybrid gene that encodes GST fused to the CelA1 sequence encoding amino acid residues 215–759 of the CelA1 protein (FIG. 5*a*). This region spans U-1 through U-4 that are suspected to be critical for UDP-glc binding. As a control, another GST fusion was created using a 1.0 kb PstI fragment that had the U-1 region deleted and might not be predicted to bind UDP-glc. The fusion proteins were overexpressed in *E. coli* purifed, and shown to have the predicted sizes of approximately 87 and 64 kD, respectively (FIG. 5*b*). The purified proteins were then subjected to SDS-PAGE, and blotted to nitrocellulose. Blotted proteins were renatured, and incubated with $^{32}$P-UDP-glc in order to test for binding (FIG. 5*b*). As predicted, the 87 kD GST-CelA1 fusion does indeed bind UDP-glc in a $Mg^{2+}$ dependent manner, while the shorter fusion with the U-1 domain deleted did not show any binding (Although not observed in the experiment shown, in some experiments very weak labeling in the presence of $Ca^{2+}$ could be observed). As further controls, note that the molecular weight standards BSA and ovalbumin, proteins lacking UDP-glc binding sites, show no interaction with UDP-glc, while phosphorylase b, an enzyme inhibited by UDP-glc (19), binds this substrate.

FIG. 6 provides the encoding sequence to the cDNA to celA1 (start ATG at~base 179), while FIG. 7 provides the encoding sequence to the approximately two-thirds 3' of the cDNA to celA2.

Example 6

Genomic DNA cDNA for the cellulose synthase clones was used to probe for genomic clones. For both, full length genomic DNA was obtained from a library made using the lambda dash 2 vector from Stratagene™, which was used to construct a genomic DNA library from cotton variety Coker 130 (*Gossypium hirsutum* cv. coker 130), using DNA obtained from germinating seedlings.

The cotton genomic library was probed with a cellulose synthase probe and genomic phage candidates were identified and purified. FIG. 8 provides an approximately 1 kb sequence of the cellulose synthase promoter region which is immediately 5' to the celA1 encoding region. The start of the cellulose synthase enzyme encoding region is at the ATG at base number 954.

Example 7

Cotton Transformation

Explant Preparation

Promoter constructs comprising the cellulose synthase promoter sequences of celAl can be cotton prepared. Coker 315 seeds are surface disinfected by placing in 50% Clorox (2.5% sodium hypochlorite solution) for 20 minutes and rinsing 3 times in sterile distilled water. Following surface sterilization, seeds are germinated in 25×150 sterile tubes containing 25 mls ½×MS salts: ½×B5 vitamins: 1.5% glucose: 0.3% gelrite. Seedlings are germinated in the dark at 28° C. for 7 days. On the seventh day seedlings are placed in the light at 28±2° C.

Cocultivation and Plant Regeneration

Single colonies of *A. tumefaciens* strain 2760 containing binary plasmids pCGN2917 and pCGN2926 are transferred to 5 ml of MG/L broth and grown overnight at 30° C. Bacteria cultures are diluted to $1\times10^8$ cells/ml with MG/L just prior to cocultivation. Hypocotyls are excised from eight day old seedlings, cut into 0.5–0.7 cm sections and placed onto tobacco feeder plates (Horsch et al. 1985). Feeder plates are prepared one day before use by plating 1.0 ml tobacco suspension culture onto a petri plate containing Callus Initiation Medium CIM without antibiotics (MS salts: B5 vitamins: 3% glucose: 0.1 mg/L 2,4-D: 0.1 mg/L kinetin: 0.3% gelrite, pH adjusted to 5.8 prior to autoclaving). A sterile filter paper disc (Whatman #1) was placed on top of the feeder cells prior to use. After all sections are prepared, each section was dipped into an *A. tumefaciens* culture, blotted on sterile paper towels and returned to the tobacco feeder plates.

Following two days of cocultivation on the feeder plates, hypocotyl sections are placed on fresh Callus Initiation Medium containing 75 mg/L kanamycin and 500 mg/L carbenicillin. Tissue is incubated at 28±2° C., 30 uE 16:8 light:dark period for 4 weeks. At four weeks the entire explant is transferred to fresh callus initiation medium containing antibiotics. After two weeks on the second pass, the callus is removed from the explants and split between Callus Initiation Medium and Regeneration Medium (MS salts: 40 mM $KNO_3$: 10 mM $NH_4Cl$:B5 vitamins:3% glucose:0.3% gelrite:400 mg/L carb:75 mg/L kanamycin).

Embryogenic callus is identified 2–6 months following initiation and was subcultured onto fresh regeneration medium. Embryos are selected for germination, placed in static liquid Embryo Pulsing Medium (Stewart and Hsu medium: 0.01 mg/l NAA: 0.01 mg/L kinetin: 0.2 mg/L GA3) and incubated overnight at 30° C. The embryos are blotted on paper towels and placed into Magenta boxes containing 40 mls of Stewart and Hsu medium solidified with Gelrite. Germinating embryos are maintained at 28±2° C. 50 uE $m^{-2}s^{-1}$16:8 photoperiod. Rooted plantlets are transferred to soil and established in the greenhouse.

Cotton growth conditions in growth chambers are as follows: 16 hour photoperiod, temperature of approximately 80–85°, light intensity of approximately 500 μEinsteins. Cotton growth conditions in greenhouses are as follows: 14–16 hour photoperiod with light intensity of at least 400 μEinsteins, day temperature 90–95° F., night temperature 70–75° F., relative humidity to approximately 80%.

Plant Analysis

Flowers from greenhouse grown Tl plants are tagged at anthesis in the greenhouse. Squares (cotton flower buds), flowers, bolls etc. are harvested from these plants at various stages of development and assayed for observable phenotype or tested for enzyme activity.

Example 8

Transformation of Tree Species

Numerous methods are known to the art for transforming forest tree species, for example U.S. Pat. No. 5,654,190 discloses a process for producing transgenic plant belonging to the genus Populus, the section Leuce.

The above results demonstrate how the cellulose synthase cDNA may be used to alter the phenotype of a transgenic plant cell, and how the promoter may be used to modify transgenic cotton fiber cells.

All publications and patent applications cited in this specification are herein incorporated by reference as if each individual publication or patent application are specifically and individually indicated to be incorporated by reference.

Although the foregoing invention has been described in some detail, by way of illustration and example for purposes of clarity and understanding, it will be readily apparent to those of ordinary skill in the art that certain changes and modifications may be made thereto, without departing from the spirit or scope of the appended claims.

What is claimed is:

1. An isolatd DNA sequence encoding a cotton cellulose synthase.

2. The DNA sequence of claim 1 wherein said cotton cellulose synthase is celA1.

3. The DNA sequence of claim 2 wherein said sequence comprises SEQ ID NO:1.

4. An isolated DNA sequence comprising the sequence set forth in SEQ ID NO:1.

5. An isolated DNA sequence consisting of the sequence set forth in SEQ ID NO:2.

6. An isolated polynucleotide comprising a sequence which encodes the sequence set forth in SEQ ID NO:6.

7. An isolated polynucleotide consisting of a sequence which encodes the sequence set forth in SEQ ID NO:7.

8. An isolated polynucleotide consisting of a sequence which encodes the sequence set forth in SEQ ID NO:8.

9. A recombinant DNA construct comprising the DNA sequence according to any one of claims 1, 2, or 3.

10. The DNA construct of claim 9 comprising a cotton fiber specific promoter operably joined to said DNA sequence.

11. A plant cell comprising the DNA construct according to claim 9.

12. A plant cell comprising the DNA construct according to claim 10.

13. A plant comprising the cell of claim 11.

* * * * *